(12) United States Patent
Cantor

(10) Patent No.: US 7,959,920 B2
(45) Date of Patent: *Jun. 14, 2011

(54) METHODS OF MAKING AND USING ANTIBODIES DIRECTED TO PARATHYROID HORMONE

(75) Inventor: Thomas L. Cantor, El Cajon, CA (US)

(73) Assignee: Scantibodies Laboratory, Inc., Santee, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/516,912

(22) Filed: Sep. 6, 2006

(65) Prior Publication Data

US 2007/0098726 A1    May 3, 2007

Related U.S. Application Data

(60) Provisional application No. 60/714,749, filed on Sep. 6, 2005.

(51) Int. Cl.
*A61K 39/395* (2006.01)
(52) U.S. Cl. .................................. 424/145.1
(58) Field of Classification Search .................. None
See application file for complete search history.

(56) References Cited

U.S. PATENT DOCUMENTS

| | | | |
|---|---|---|---|
| 4,369,138 A | 1/1983 | Lindall | |
| 6,030,790 A | 2/2000 | Adermann et al. | |
| 6,689,566 B1 | 2/2004 | Cantor et al. | |
| 6,743,590 B1 | 6/2004 | Cantor et al. | |
| 6,838,264 B2 | 1/2005 | Zahradnik et al. | |
| 2004/0219598 A1 | 11/2004 | Cantor | |
| 2005/0202506 A1* | 9/2005 | Cantor | 435/7.1 |

FOREIGN PATENT DOCUMENTS

WO    WO 03/003986 A2 *   1/2003

OTHER PUBLICATIONS

John et al., (The Journal of Clinical Endocrinology & Metabolism, vol. 84, No. 11, pp. 4287-4290, 1999).*
Mohan et al. Bone 2000, 27:471-478.*
Berson et al., J. Clin. Invest. (1956) 35:170-190.
Berson et al., PNAS USA (1963) 49:613-617.
Broadus et al., J. Clin. Invest. (1977) 60:771-783.
Brossard et al., Clin. Chem. (2000) 46(5):697-703.
Brossard et al., J. Bone and Miner. Res. (1999) 14:S444.
Canterbury et al., J. Clin. Invest. (1975) 55:1245-1253.
Dambacher et al., Clinical Science (1979) 57:435-443.
Endres et al., Kidney International (1982) 21:132.
Flueck et al., Proceedings of the 58th American Meeting of the Endocrine Society, Jun. 1976.
Freitag et al., New England Journal of Medicine (1978) 298:29-32.
Gallagher et al., J. Lab. Clin. Med. (1980) 95:373-385.
Gao et al., Clinica Chimica Acta (1996) 245:39-59.
Gao et al., J. Bone and Miner. Res. (1999) 14:S446.
Goltzman et al., J. Clin. Invest. (1980) 65:1309-1317.
Habener and Potts, New England Journal of Medicine (1978) 299:580-585, 635-644.
John et al., J. Clin. Endocrin. & Metab. (1999) 84:4287-4290.
Kao et al., Clin. Chem. (1982) 28:69-74.
Keutmann et al., Biochemistry (1978) 17:5723-5729.
Kohler and Milstein, Nature (1975) 256:495-497.
Lafferty, Medicine (1966) 45:247-260.
Lepage et al., Clin. Chem. (1998) 44:805-809.
Mallette et al., J. Clin. Endocrinology Metab. (1982) 54:1017-1024.
Mallette, Ligand Review (1979) 1:18-19.
Nussbaum et al., Clin. Chem. (1988) 33(8):1364-1367.
Raisz et al., Annals International Medicine (1979) 91:739-740.
Rodbard and Hutt, "Statistical Analysis of Radioimmunoassays and Immunoradiometric (labeled antibody) Assays" in Assays, Radioimmunoassays and Related Procedures in Medicine, vol. 1, Vienna: International Atomic Energy Agency, Vienna, (1974) pp. 165-192.
Rodbard et al. J. Clin. Endocrinology Metab. (1968) 28:1412-1418.
Roos et al., J. Clin. Endocrinology and Metab. (1981) 53:709-721.
Segre et al., American Journal of Medicine (1974) 56:774-784.
Segre et al., Biochemistry (1977) 16:2417-2427.
Segre et al., J. Clin. Invest. (1981) 67:439-448.
Segre et al., J. Clin. Invest. (1981) 67:449-457.
Segre et al., J. Clin. Invest. (1972) 51:3163-3172.
Silverman and Yalow, J. Clin. Invest. (1973) 52:1958-1971.
Slatopolsky et al., Journal of American Society of Nephrology (1999) 10:625A.
Travis, (ed.), "Clinical Radioimmunoassay" in State-of-the-Art Scientific Newsletter, Inc., Anaheim, CA 92803, (1980) pp. 13-16.
Watson et al., Molecular Biology of the Gene, 4th edition, (1987) The Bejamin/Cummings Pub. Co., p. 224.
Wood et al., J. Clin. Chem. Biochemistry (1980) 18:789-795.
Wood et al., PNAS USA (1985) 82:1585-1588.
Woodhead, Clin. Biochem. (1990) 23:17-21.

* cited by examiner

*Primary Examiner* — Sharon Wen
(74) *Attorney, Agent, or Firm* — Morrison & Foerster LlP

(57) ABSTRACT

The present invention relates to methods of generating anti-PTH antibodies and antibodies generated by the methods of the invention. The anti-PTH antibodies generated by the methods of the invention specifically bind to an epitope on a whole PTH (1-84) which includes one or more N-terminal amino acid residues of the whole PTH. The anti-PTH antibodies generated are useful for detecting whole PTH in a biological sample and for diagnosing parathyroid diseases or disorders.

3 Claims, 6 Drawing Sheets

Representative Standard Curve

SEQUENCE LISTING

<160> NUMBER OF SEQ ID NOS: 1

<210> SEQ ID NO 1
<211> LENGTH: 84
<212> TYPE: PRT
<213> ORGANISM: Homo sapiens

```
<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asn Lys Ala Asp Val Asn Val Leu Thr Lys
65                  70                  75                  80

Ala Lys Ser Gln
```

METHODS OF MAKING AND USING ANTIBODIES DIRECTED TO PARATHYROID HORMONE

CROSS-REFERENCE TO RELATED APPLICATIONS

This application claims the benefit of U.S. Provisional Application Ser. No. 60/714,749, filed Sep. 6, 2005. The contents of this application are hereby incorporated by reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 532212003500Seqlist.txt | Sep. 26, 2008 | 1,120 bytes |

FIELD OF THE INVENTION

The present invention relates to methods of generating antibodies specific for parathyroid hormone, novel compositions, methods and kits for differentiating parathyroid diseases in a subject. These compositions, methods and kits can be used, for example to differentiate hyperparathyroidism, hypoparathyroidism, high bone turnover, and adynamic bone disease from normal or non-disease states.

BACKGROUND OF THE INVENTION

Calcium plays an indispensable role in cell permeability, the formation of bones and teeth, blood coagulation, transmission of nerve impulse, and normal muscle contraction. The concentration of calcium ions in the blood is, along with calcitrol and calcitonin, regulated mainly by parathyroid hormone (PTH). Although calcium intake and excretion may vary, PTH serves through a feedback mechanism to maintain a steady concentration of calcium in cells and surrounding fluids. When serum calcium decreases, the parathyroid glands secrete PTH, affecting the release of the stored calcium. When serum calcium increases, stored calcium release is retarded through lowered secretions of PTH.

The complete form of human PTH (hPTH) is a unique 84 amino acid peptide (SEQ ID NO:1) as is shown in FIG. 1 of U.S. Pat. No. 6,743,590 and U.S. Application Pub. No. 2004/0219598A1. Researchers have found that this peptide has an anabolic effect on bone that involves a domain for protein kinase C activation (amino acid residues 28 to 34) as well as a domain for adenylate cyclase activation (amino acid residues 1 to 7). However, the various catabolic forms of clipped or fragmented PTH peptides, also found in circulation, are most likely formed by intraglandular or peripheral metabolism. For example, whole PTH can be cleaved between amino acids 34 and 35 to produce a (1-34) PTH N-terminal fragment and a (35-84) PTH C-terminal fragment. Likewise, clipping can occur between either amino acids 36 and 37 or 37 and 38. Recently, a large PTH fragment referred to as "non-(1-84) PTH" has been disclosed which is clipped closer to the N-terminal end of PTH. (See LePage, R., et al., Clin. Chem. 44: 805-810 (1998)).

The clinical need for accurate measurement of PTH is well demonstrated. Serum PTH level is one of the most important indexes for patients with the following diseases: familial hypocalciuric hypercalcemia; multiple endocrine neoplasia types I and II; osteoporosis; Paget's bone disease; primary hyperparathyroidism—caused by primary hyperplasia or adenoma of the parathyroid glands; pseudohypoparathyroidism; and renal failure, which can cause secondary hyperparathyroidism.

PTH plays a role in the course of disease in a patient with chronic renal failure. Renal osteodystrophy (RO) is a complex skeletal disease comprising osteitis fibrosa cystica (caused by PTH excess), osteomalacia—unmineralized bone matrix (caused by vitamin D deficiency), extraskeletal calcification/ossification (caused by abnormal calcium and phosphorus metabolism), and adynamic bone disease (contributed to by PTH suppression). Chronic renal failure patients can develop RO. Failing kidneys increase serum phosphorus (hyperphosphoremia) and decrease 1,25-dihydroxyvitamin D (1,25-D) production by the kidney. The former results in secondary hyperparathyroidism from decreased gastrointestinal calcium adsorption and osteitis fibrosa cystica from increased PTH in response to an increase in serum phosphorus. The latter causes hypocalcemia and osteomalacia. With the onset of secondary hyperparathyroidism, the parathyroid gland becomes less responsive to its hormonal regulators because of decreased expression of its calcium and vitamin D receptors. Serum calcium drops. RO can lead to digital gangrene, bone pain, bone fractures and muscle weakness.

Determining circulating biologically active PTH levels in humans has been challenging. One major problem is that PTH is found at low levels, normally 10 pg/mL to 40 pg/mL (i.e., 1 pmol/L to 4 pmol/L). Coupled with extremely low circulating levels is the problem of the heterogeneity of PTH and its many circulating fragments. In many cases, immunoassays have faced substantial and significant interference from circulating PTH fragments. For example, some commercially available PTH kits have almost 100% cross-reactivity with the non-(1-84) PTH fragment. See the LePage article supra.

PTH immunoassays have varied over the years. One early approach is a double antibody precipitation immunoassay found in U.S. Pat. No. 4,369,138, issued to Arnold W. Lindall et alia. A first antibody has a high affinity for a $PTH_{65-84}$ fragment. A radioactive labeled (65-84) PTH peptide is added to the sample with the first antibody to compete for the unlabeled peptide. A second antibody is added which binds to any first antibody and PTH fragment complex, thereby forming a precipitate. Both precipitate and supernatant can be measured for radioactive activity, and PTH levels can be calculated therefrom.

In an effort to overcome PTH fragment interference, immunoradiometric two-site assays for intact PTH (I-PTH) have been introduced, such as Allegro® Intact PTH assay by the Nichols Institute of San Juan Capistrano, Calif. In one version, a capture antibody specifically binds to the C-terminal portion of hPTH while a labeled antibody specifically binds to the N-terminal portion of the captured hPTH. In another, two monoclonal antibodies were used, both of which attached to the N-terminal portion of hPTH. (For the purposes of the present disclosure, the complete form of human PTH is referred to as "whole PTH" or "wPTH" as distinguished from "intact PTH" or "I-PTH" which can include not only wPTH, but also a large PTH fragment cleaved about amino acids 5 to 8.) Unfortunately, these assays have problems in that they measure but do not discriminate between w-PTH and I-PTH. This inability comes to the fore in hyperparathyroid patients and renal failure patients who have significant endogenous concentrations of large, non-whole PTH fragments.

Researchers have recently, made a specific binding assay directed to the large N-terminal PTH fragments. See Gao, P., et al., *Clinica Chimica Acta* 245: 39-59 (1996). This immunochemiluminometric assay uses two monoclonal antibodies to detect N-terminal (1-34) PTH fragments but not mid-portion PTH fragments or C-terminal PTH fragments. A key factor in the design of these assays is to eliminate any reaction with C-terminal PTH fragments.

Several PTH assay systems have been described. See, e.g., U.S. Pat. Nos. 6,743,590; 6,689,566; 6,838,264; 6,030,790; U.S. Pub. No. 2004/0219598A1.

An important discovery is that adynamic bone loses its capacity to buffer calcium and phosphate as the bones are shut down. Subjects afflicted with such conditions are unable to effectively buffer calcium as it enters their bodies through their diet. This calcium enters the blood stream and is thereafter shuttled to the soft tissues. The parathyroid gland is particularly subject to, and detrimentally affected by, this influx of calcium and thereby produces PTH fragments (one of which is $PTH_{7-84}$, which is active in a counter-regulatory direction) rather than, or in addition to, the active $PTH_{1-84}$ (SEQ ID NO:1) (which is whole PTH). Accordingly, in subjects with adynamic bone, the concentration and production of PTH fragments is increased. In light of this and other related information, the measurement of PTH fragment levels, and particularly in conjunction with the measurement of whole PTH, can be used effectively to differentiate subjects having adynamic bone versus those having normal bone and high bone turnover rates.

There is a tremendous need to be able to non invasively separate the dialysis patients with ABD (Adynamic bone disease) from those suffering from high bone turnover to avoid over treatment of ABD dialysis patients. Over treatment of dialysis patients with ABD is a frequent occurrence under presently utilized methods. For example, package inserts that prescribe the use of Zemplar® (paricalcitol injection) and Calcijex® (calcitriol injection) are being used to treat thousands of dialysis patients that stand a great risk of over treatment under the prescribed protocols that do not account for circulating PTH fragment levels that are in some cases non active and in some case possessing counter regulatory biological activity such as $PTH_{7-84}$. The present invention addresses these and other needs in the art.

BRIEF SUMMARY OF THE INVENTION

In one aspect, the present invention provides a method of generating an antibody that specifically binds to a parathyroid hormone (PTH) peptide, said method comprising: a) introducing a PTH peptide immunogen to a mammal in an amount sufficient to produce an antibody to said PTH peptide immunogen; wherein said PTH peptide immunogen has an amino acid sequence which starts at amino acid position 1 and ends at any amino acid position ranging from 34 to 84 of a whole PTH; b) recovering said antibody from said mammal; c) purifying said antibody by a combination of a positive adsorption to a PTH peptide (the positive adsorption PTH peptide) having an amino acid sequence which starts at amino acid position 1 or 2, or at any position selected from positions 1, 2, 3, 4, 5, 6, 7, 8 and 9 of a whole PTH; and ends at any amino acid position ranging from 4 to 84 of said whole PTH, and a negative adsorption to a PTH peptide having an amino acid sequence which starts at any amino acid position ranging from 2 to 20 and ends at any amino acid position ranging from 6 to 84 of said whole PTH, provided that the PTH peptide used for the negative adsorption (negative adsorption PTH peptide) purification process is missing at least one N-terminal amino acid that is present in the positive adsorption PTH peptide, and provided that each PTH peptide has a minimum length of at least 4 amino acids. In some embodiments, the negative adsorption process uses a PTH peptide that is truncated at its N-terminal end by one amino acid more than the PTH peptide used for the positive adsorption process; in some embodiments, the negative adsorption uses a PTH peptide that is truncated by 2, or by 3, or by 4, or by 5, or by 6, amino acids more than the PTH peptide used for the positive adsorption.

In some embodiments, the purification step c) uses a combination of a positive adsorption to a PTH peptide having an amino acid sequence which starts at amino acid position 1 and ends at any amino acid position ranging from 4 to 84, or from 6 to 84, of said whole PTH, and a negative adsorption to a PTH peptide having an amino acid sequence which starts at any amino acid position ranging from 2 to 20, or from 2 to 7, and ends at any amino acid position ranging from 6 to 84, or from 16 to 84, of said whole PTH, provided that each PTH peptide (positive adsorption PTH peptide or negative adsorption PTH peptide) has a minimum length of at least 4 amino acids.

In other embodiments, the purification step c) uses a combination of a positive adsorption to a PTH peptide having an amino acid sequence which starts at amino acid position 2 and ends at any amino acid position ranging from 4 to 84, or from 16 to 84, of said whole PTH, and a negative adsorption to a PTH peptide having an amino acid sequence which starts at any amino acid position ranging from 3 to 20, or from 3 to 7, and ends at any amino acid position ranging from 6 to 84, or from 16 to 84, of said whole PTH, provided that each PTH peptide has a minimum length of at least 4 amino acids.

In some embodiments, the positive adsorption to a PTH peptide in the purification process described as step c) is performed before the negative adsorption to a PTH peptide described in step c).

In some embodiments, the positive adsorption to a PTH peptide in the purification process described as step c) is performed after the negative adsorption to a PTH peptide described in step c).

In some embodiments, said PTH peptide used for the positive adsorption ends at the same amino acid position as said PTH peptide used for the negative adsorption. In some embodiments, the PTH peptide used for the negative adsorption in the purification step is truncated at the N-terminal by one amino acid more than is the PTH peptide used for the positive adsorption, i.e., the PTH peptide used for the negative adsorption starts one amino acid residue later in the PTH sequence than does the PTH peptide used for the positive adsorption. In some embodiments, the PTH peptide immunogen in step a) is $PTH_{1-34}$ or $PTH_{1-84}$ (SEQ ID NO:1). In some embodiments, the whole PTH is a mammalian PTH (such as a human PTH). In some embodiments, the PTH peptide for the positive adsorption in step c) is $PTH_{1-34}$. In some embodiments, the PTH peptide for the negative adsorption in step c) is $PTH_{2-34}$.

In some embodiments, the antibody generated binds to said PTH peptide immunogen with higher affinity than said antibody binds to a PTH peptide contained within said PTH peptide immunogen, i.e., the antibody binds more tightly to the immunogen than to any truncated form of the immunogen.

In another aspect, the invention provides an isolated anti-PTH antibody generated by the methods described herein. In some embodiments, the isolated antibody does not specifically bind to a PTH peptide selected from the group consisting of $PTH_{1-5}$, $PTH_{1-6}$, $PTH_{1-7}$, $PTH_{1-8}$, $PTH_{1-9}$, $PTH_{1-10}$, $PTH_{1-12}$, $PTH_{1-15}$, $PTH_{2-12}$ and $PTH_{2-15}$. The epitope that the anti-PTH antibody binds to may be a linear epitope or a conformational epitope. In some embodiments, the isolated antibody binds to an epitope which includes the first N-terminal amino acid of the whole PTH. In some embodiments, the isolated antibody binds to an epitope which includes the second N-terminal amino acid of the whole PTH. In some embodiments, the isolated antibody binds to an epitope which includes the first and the second N-terminal amino acids of the whole PTH. In some embodiments, the isolated antibody is capable of detecting the whole PTH at a physiological level in a mammalian sample, with a proviso that the isolated antibody avoids binding to a non-whole PTH fragment. In some embodiments, the isolated antibody is capable of detecting the level of whole parathyroid hormone that is less than 4 pmol/L in a sample. In some embodiments, the isolated antibody specifically binds to human whole PTH. In some embodiments, the antibody is a goat polyclonal antibody.

In another aspect, the invention also provides a method for measuring whole parathyroid hormone (PTH) in a mammalian sample, which method comprises: a) obtaining a sample from a mammal to be tested; b) contacting said sample with the isolated antibody generated according to the methods described herein; and c) assessing a complex formed between said whole parathyroid hormone, if present in said sample, and said antibody, to measure the level of said whole parathyroid hormone in said mammalian sample.

In some embodiments, the method is used for clinical management of renal disease subjects afflicted with osteoporosis or diagnosing primary hyperparathyroidism.

In some embodiments, the mammal is a human. In some embodiments, the whole PTH at a physiological level in a mammalian sample is detected. In some embodiments, the level of whole parathyroid hormone measured is less than 4 pmol/L.

In some embodiments, the complex is assessed by a sandwich or competitive assay format.

In some embodiments, the method further comprises measuring a PTH peptide fragment level and/or total PTH level. In some embodiments, the method further comprises comparing at least two parameters selected from the group consisting of the whole PTH level, total PTH peptide fragment level, total PTH level, C-terminal PTH fragment (cPTH) level, N-terminal PTH fragment level and mid-terminal PTH fragment (mPTH) level. In some embodiments, the results of the comparison are used to determine whether the mammal suffers from a bone turnover related disorder, or to monitor bone disease or disorder related treatment.

In some embodiments, the method is used in the diagnosis or monitoring of treatment for adynamic bone disease (ABD) or severe hyperparathyroidism. In some embodiments, the method is used for: a) differentiating between a person having substantially normal parathyroid function and having hyperparathyroidism; b) monitoring parathyroid related bone disease and treatment; c) monitoring effects of therapeutic treatment for hyperparathyroidism; or d) diagnosing parathyroid related bone disease.

In another aspect, the invention also provides a kit for generating an antibody that specifically binds to a parathyroid hormone (PTH) peptide, said kit comprising: a) an isolated PTH peptide having an amino acid sequence which starts at amino acid position 1 and ends at any amino acid position ranging from 34 to 84 of a whole PTH; b) means for introducing said isolated PTH peptide in a) to a mammal in an amount sufficient to produce an antibody to said PTH peptide; c) a resin bound with a second PTH peptide at least four amino acids in length having an amino acid sequence which starts at amino acid position 1 or 2 and ends at any amino acid position ranging from 4 to 84, or from 16 to 84 of said whole PTH; and d) a resin immobilized with a third PTH peptide at least four amino acids in length having an amino acid sequence which starts at any amino acid position ranging from 2 to 20, or from 2 to 7, and ends at any amino acid position ranging from 6 to 84, or from 16 to 84, of the whole PTH; provided that the N-terminal end of the third PTH peptide in item c) starts at least one amino acid position later in the PTH sequence than the second PTH peptide in item d) does. In some embodiments, the PTH peptide in d) ends at the same amino acid position as said PTH peptide in c).

In another aspect, the invention also provides a kit for measuring a whole parathyroid hormone in a mammalian sample, which kit comprises, in a container, the isolated antibody generated according to the methods described herein.

DETAILED DESCRIPTION OF THE INVENTION

A. Definitions

Figure 1:
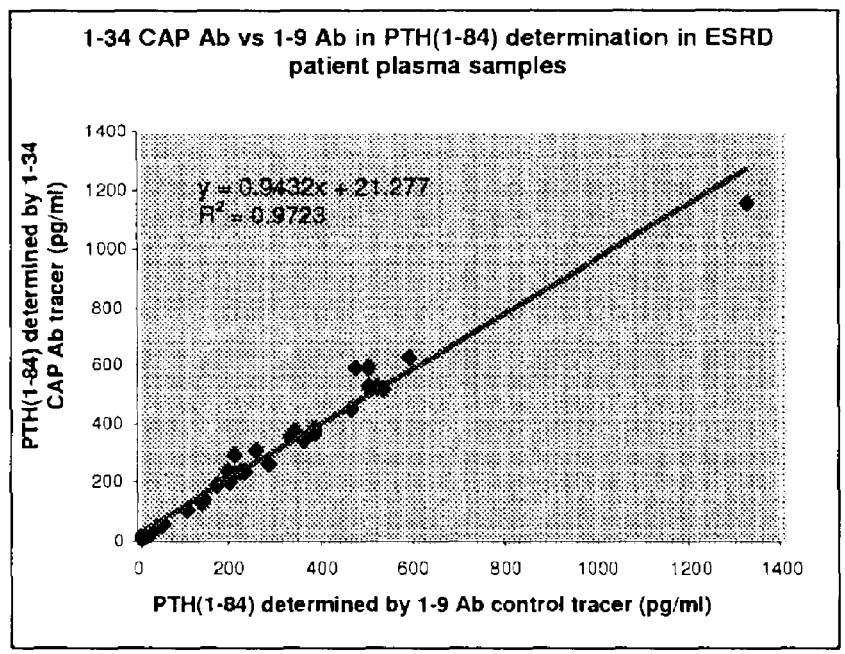
FIG. 1 is a graph showing the correlation between using the $PTH_{1-34}$ CAP antibody (negatively adsorbed with $PTH_{2-34}$ at room temperature for 3.5 hours using a batch method in which the $PTH_{2-34}$ was attached to a solid phase resin) and the anti-$PTH_{1-9}$ antibody (that was produced by affinity purifying a $PTH_{1-84}$ antibody using a $PTH_{1-9}$ peptide with a cysteine in the $10^{th}$ amino acid position, which was attached to a solid phase resin) as tracer for wPTH determination in 40 ESRD (End Stage Renal Disease) patients as described in the SLI (Scantibodies Laboratories, Inc., Santee, Calif.) Directional Insert 3KI037 v.6, which is presented as Example 6.

Unless defined otherwise, all technical and scientific terms used herein have the same meaning as is commonly understood by one of ordinary skill in the art to which this invention belongs. All patents, patent applications (published or unpublished) and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "antibody" is used in the broadest sense. Therefore, an "antibody" can be naturally occurring or man-made such as monoclonal antibodies produced by conventional hybridoma technology and/or a functional fragment thereof. Antibodies of the present invention comprise monoclonal and polyclonal antibodies as well as fragments (such as Fab, Fab', F(ab')$_2$, Fv) containing the antigen-binding domain and/or one or more complementary determining regions of these antibodies.

As used herein, "monoclonal antibody" refers to an antibody obtained from a population of substantially homogeneous antibodies, i.e., the antibodies comprising the population are identical except for possible naturally occurring mutations that are present in minor amounts. As used herein, a "monoclonal antibody" further refers to functional fragments of monoclonal antibodies.

As used herein, "mammal" refers to any of the mammalian class of species, preferably human (including humans, human subjects, or human patients). Mammals include, but are not limited to, farm animals, sport animals, pets, primates, horses, dogs, cats, mice and rats.

As used herein, "whole parathyroid hormone (PTH)" or "wPTH" refers to the complete molecule of PTH. This term is not species-specific unless otherwise designated. For purposes herein, the name "parathyroid hormone (PTH)" is used herein, although all other names are contemplated. It is intended to encompass whole PTH with conservative amino acid substitutions that do not substantially alter the biological activity of $PTH_{1-84}$ (SEQ ID NO:1). Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., MOLECULAR BIOLOGY OF THE GENE, 4th Edition, 1987, The Benjamin/Cummings Pub. Co., p. 224).

As used herein, "parathyroid hormone (PTH) agonist," "cyclase activating PTH" or "CAP" refers to the complete molecule of PTH or a fragment, derivative or analog thereof that stimulates osteoclast formation and bone turnover to increase blood calcium levels. PTH agonist further refers to peptides which have PTH agonist properties. Other names of PTH include parathormone and parathyrin. For purposes herein, the name "parathyroid hormone (PTH)" is used herein, although all other names are contemplated. It is intended to encompass PTH agonist with conservative amino acid substitutions that do not substantially alter its biological activity from the biological activity of $PTH_{1-84}$ (SEQ ID NO:1). Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., MOLECULAR BIOLOGY OF THE GENE, 4th Edition, 1987, The Benjamin/Cummings Pub. co., p. 224). PTH agonist assay values may be obtained by measuring a sample with a Scantibodies Whole PTH Assay (Scantibodies, Santee, Calif., CAP Assay, a 3$^{rd}$ generation PTH Assay) or a Nichols (San Clemente, Calif.) BioIntact PTH assay or an Immutopics (San Clemente, Calif.) Human Bioactive PTH assay.

As used herein, the term "total PTH" refers to a total accounting of whole PTH levels in addition to PTH fragment levels. Moreover, this term is not species-specific unless otherwise designated.

As used herein, the term "PIN" refers to PTH fragments that have PTH antagonistic or inhibiting properties. For example, fragments that exhibit biological activity consistent with resulting in hypocalcemia, decrease in osteoclast formation and/or lowering of bone turnover. Therefore, although occasionally of concurrent scope, a reference to PTH fragments, as provided herein, is not intended to be limited to PIN.

As used herein, a "PTH fragment" is a PTH peptide that comprises a non-whole contiguous portion of an entire PTH protein. A reference to a PTH fragment as herein includes C-terminal, mid-terminal fragments and PIN, unless otherwise indicated. Moreover, this term is not species-specific unless otherwise designated. A PTH peptide comprises a partial or complete PTH sequence, and is often described by reference to the amino acids of a whole PTH that the PTH peptide contains. For example, $PTH_{1-34}$ refers to a peptide consisting of the first 34 amino acid residues of a PTH, and is sometimes written as PTH(1-34).

The meaning of the term anti-$PTH_{1-9}$ antibody as used in this description is meant to define a $PTH_{1-84}$ antibody with a tendency to bind $PTH_{1-84}$ (SEQ ID NO:1) in the 1-9 region where it is not uncommon for this antibody to have a higher affinity for its immunogen (1-84 PTH) compared to the PTH peptide used for affinity purification (1-9 PTH).

As used herein, "treatment" refers to any manner in which the symptoms of a condition, disorder or disease are ameliorated or otherwise beneficially altered. Treatment also encompasses any pharmaceutical use of the compositions herein.

As used herein, "disease or disorder" refers to a pathological condition in an organism resulting from, e.g., infection or genetic defect, and characterized by identifiable symptoms.

As used herein, "high bone turnover" refers to the bone turnover rate as being above a normal bone turnover rate in a subject and is one of the symptoms manifested in subjects having hyperparathyroidism. While not bound by theory, a subject afflicted with severe hyperparathyroidism has a higher bone turnover rate than the same subject afflicted with mild or moderate hyperparathyroidism, however, both having a high bone turnover rate as compared with a normal subject with normal bone turnover or with a subject afflicted with adynamic bone disease.

As used herein, the term "subject" is not limited to a specific species or sample type. For example, the term "subject" may refer to a patient, and frequently a human patient. However, this term is not limited to humans and thus encompasses a variety of mammalian species.

As used herein, "afflicted" as it relates to a disease or disorder refers to a subject having or directly affected by the designated disease or disorder.

As used herein the term "sample" refers to anything which may contain an analyte for which an analyte assay is desired. The sample may be a biological sample, such as a biological fluid or tissue. Examples of biological fluids include urine, blood, blood plasma, blood serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries, veins and individual cell(s).

As used herein the term "avoids binding" refers to the specificity of particular antibodies or antibody fragments. Antibodies or antibody fragments that avoid binding a particular moiety generally bind to their antigen with such specificity that a large percentage of the particular moiety would not be bound by such antibodies or antibody fragments. This percentage generally lies within the acceptable cross reactivity percentage with interfering moieties of assays utilizing antibodies directed to detecting a specific target. Frequently, antibodies or antibody fragments of the present disclosure avoid binding greater than about 90% of an interfering moiety, although higher percentages are clearly contemplated and preferred. For example, antibodies or antibody fragments of the present disclosure avoid binding about 91%, about 92%, about 93%, about 94%, about 95%, about 96%, about 97%, about 98%, about 99%, and about 99% or more of an interfering moiety. Less occasionally, antibodies or antibody fragments of the present disclosure avoid binding greater than about 70%, or greater than about 75%, or greater than about 80%, or greater than about 85% of an interfering moiety. Although not bound by theory, as contemplated herein, an interfering moiety may comprise a non-whole PTH fragment.

As used herein the term "physiological level of whole PTH" generally refers to the average concentration of whole PTH present in a mammal, e.g., a human, expressed in pmol/L, or another suitable measurement unit (e.g., pgm/ml). See, e.g., Woodhead, *J. S., Clin. Biochem.* 23, 17 (1990). In one aspect, the physiological range of whole PTH is between about 0.2 pmol/L to about 4 pmol/L, or about 2 pgm/ml to about 40 pgm/ml. On occasion, the physiological range of whole PTH is between about 7 pgm/ml to about 39 pgm/ml. Although specific ranges are described herein as representative of a physiological range, one of skill in the art would understand that the physiological level of whole PTH may lie outside of the presently disclosed ranges in certain subjects, as differences in assay calibration and PTH antigens used for calibration may account for some differences. Nevertheless, the compositions and methods provided herein are useful to detect discreet concentrations of whole PTH and have sensitivities within the physiological range as provided herein.

As used herein, the term "N-terminal" refers to the amino terminus of a PTH polypeptide having a free amino group. With reference to a PTH fragment, an N-terminal PTH fragment refers to a non-whole contiguous portion of PTH having an intact N-terminal portion. An "intact N-terminal" as used herein refers to PTH or a PTH fragment having an intact $1^{st}$ amino acid position of $PTH_{1-84}$ (SEQ ID NO:1). This first position is also referred to herein as an "original N-terminus" or an "original N-terminal" amino acid.

As used herein, the term "C-terminal" refers to the carboxyl terminus of a PTH polypeptide having a free carboxyl group. With reference to a PTH fragment, a C-terminal PTH fragment refers to a non-whole contiguous portion of PTH having an intact C-terminal. An "intact C-terminal" as used herein refers to PTH or a PTH fragment having an intact 84th position of $PTH_{1-84}$ (SEQ ID NO:1). This 84th amino acid position is also referred to herein as an "original C-terminus" or an "original C-terminal" amino acid.

As used herein, the term "mid-terminal PTH fragment" refers to a non-whole contiguous portion of PTH having neither an intact N-terminal nor an intact C-terminal. These types of PTH fragments may also be referred to herein as "mid-terminus fragments."

As used herein, the term "specifically binds" refers to the specificity of an antibody such that it preferentially binds to a defined target. An antibody "specifically binds" to a target if it binds with greater affinity, avidity, more readily, and/or with greater duration than it binds to other substances. For example, an antibody that specifically binds to a target may bind to the target with at least about 10%, at least about 20%, at least about 30%, at least about 50%, at least about 60%, at least about 70%, at least about 80%, at least about 90%, or more, greater affinity as compared to binding to other substances; or with at least about two-fold, at least about five-fold, at least about ten-fold, or more of the affinity for binding to other substances. Recognition by an antibody of a particular target in the presence of other potential targets is one characteristic of such binding. Specific binding of the presently contemplated antibodies to particular PTH targets is measured through known methods utilizing the tools provided herein.

As used herein, "stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see CURRENT PROTOCOLS IN MOLECULAR BIOLOGY (Ausubel et al. eds., Wiley Interscience Publishers, 1995); MOLECULAR CLONING: A LABORATORY MANUAL (J. Sambrook, E. Fritsch, T. Maniatis eds., Cold Spring Harbor Laboratory Press, 2d ed. 1989); Wood et al., *Proc. Natl. Acad. Sci. USA*, 82:1585-1588 (1985).

As used herein the term "isolated" refers to material removed from its original environment, and is altered from its natural state. For example, an isolated polypeptide could be coupled to a carrier, and still be "isolated" because that polypeptide is not in its original environment.

As used herein, the phrase "positive adsorption" usually refers to a purification method wherein the substance being purified has an affinity for a specified immobilized species (this is not to imply that the substance preferentially binds the specified immobilized species over the immunogen, only that it has a useful level of affinity for the positive adsorption species). Exposure of the substance being purified to the immobilized species results in at least partial temporary immobilization of the substance, permitting removal of at least some other substances and effecting at least partial purification. Similarly, the phrase "negative adsorption" usually refers to a purification method wherein the substance being purified (which does not bind significantly to the specified immobilized species during the negative adsorption process) has little affinity for a specified immobilized species, but at least one impurity expected to be present in the substance has a specific affinity for the immobilized species. Exposure of the substance being purified to the immobilized species results in at least partial immobilization of at least one such impurity, permitting at least partial and preferably substantially complete removal of at least one such impurity, thus effecting at least partial purification of the substance of interest.

The present disclosure encompasses antigens, antibodies and methods of producing and isolating antibodies that have a particular specificity to target proteins and/or peptides which contain a specific amino acid residue or multiple amino acid residues, in a series or otherwise. The specific amino acid residue(s) may be located in the N-terminal region of a protein or peptide or in the C-terminal region. Moreover the specific amino acid residue(s) may be located in a region between the N-terminal and C-terminal regions of a protein or peptide. Occasionally, when there is more than one specific amino acid residue, such residues may be dispersed in any one or more of the N-terminal, C-terminal, between these two regions, and/or in all of these regions.

In disclosing the present invention, one should remember that there are a number of closely analogous, species dependent forms of PTH. For rat PTH, mouse PTH, bovine PTH, canine PTH, horse PTH or porcine PTH, for example, one finds the substitutions at some of the amino acids in the human or animal hPTH sequences. For the purposes of the present invention, one can interchangeably use antibodies or antibody fragments to forms of these PTHs from various species, although it is preferred to use an antibody with specificity for PTH having a sequence matching the species in which the PTH measurements are made.

B. Methods of Making Anti-PTH Antibodies that Specifically Bind to an Epitope that Includes N-terminal Amino Acids of a Whole PTH and Antibodies Generated by the Methods The present invention provides a method of generating an antibody that specifically binds to a parathyroid hormone (PTH) peptide, said method comprising: a) introducing a PTH peptide immunogen to a mammal in an amount sufficient to produce an antibody to said PTH peptide immunogen; wherein said PTH peptide immunogen has an amino acid sequence which starts at amino acid position 1 and ends at any amino acid position ranging from 34 to 84 of a whole PTH; b) recovering said antibody from said mammal; c) purifying said antibody by a combination of a positive adsorption to a PTH peptide having an amino acid sequence which starts at amino acid position 1 or 2 and ends at any amino acid position ranging from 4 to 84, or from 16 to 84, of said whole PTH, and a negative adsorption to a PTH peptide having an amino acid sequence which starts at any amino acid position ranging from 2 to 20, or from 2 to 7, and ends at any amino acid position ranging from 16 to 84 of said whole PTH. In each case, the PTH peptides used for the positive and negative adsorption typically refer to an immobilized peptide that is at least four amino acids in length, and preferably is at least 5 or at least 6 amino acids in length. The PTH peptide used for the negative adsorption is commonly truncated at its N-terminal end by at least one amino acid more than is the PTH peptide used for the positive adsorption; thus if the positive adsorption uses a peptide that begins at position 1 of a PTH, the negative adsorption uses a PTH peptide that begins at position 2 or later; and if the positive adsorption uses a peptide that begins at position 2 of a PTH, the negative adsorption uses a PTH peptide that begins at position 3 or later in the PTH sequence. In some embodiments, the positive adsorption is performed before the negative adsorption in step c). In some embodiments, the negative adsorption is performed before the positive adsorption in step c). In some embodiments; said PTH peptide used for the positive adsorption in step c) ends at the same amino acid position as said PTH peptide used for the negative adsorption in step c).

To generate the anti-PTH antibody, a PTH peptide having an intact N-terminal sequence as a part of an immunogen for injection into a mammal (such as a goat) may be used. Any PTH peptide ranging from $PTH_{1-34}$ to $PTH_{1-84}$ (SEQ ID NO:1) may be utilized; for example, $PTH_{1-34}$, $PTH_{1-35}$, $PTH_{1-36}$, $PTH_{1-37}$, $PTH_{1-38}$, $PTH_{1-39}$, $PTH_{1-40}$, $PTH_{1-41}$, $PTH_{1-42}$, $PTH_{1-43}$, $PTH_{1-44}$, $PTH_{1-45}$, $PTH_{1-46}$, $PTH_{1-47}$, $PTH_{1-48}$, $PTH_{1-49}$, $PTH_{1-50}$, $PTH_{1-51}$, $PTH_{1-52}$, $PTH_{1-53}$, $PTH_{1-54}$, $PTH_{1-55}$, $PTH_{1-56}$, $PTH_{1-57}$, $PTH_{1-58}$, $PTH_{1-59}$, $PTH_{1-60}$, $PTH_{1-61}$, $PTH_{1-62}$, $PTH_{1-63}$, $PTH_{1-64}$, $PTH_{1-65}$, $PTH_{1-66}$, $PTH_{1-67}$, $PTH_{1-68}$, $PTH_{1-69}$, $PTH_{1-70}$, $PTH_{1-71}$, $PTH_{1-72}$, $PTH_{1-73}$, $PTH_{1-74}$, $PTH_{1-75}$, $PTH_{1-76}$, $PTH_{1-77}$, $PTH_{1-78}$, $PTH_{1-79}$, $PTH_{1-80}$, $PTH_{1-81}$, $PTH_{1-82}$, $PTH_{1-83}$, and $PTH_{1-84}$ (SEC) ID NO:1) may be used. The PTH may be any mammalian PTH, including human, rat, mouse, bovine, canine, porcine, and horse. PTH sequences for these mammalian species are known in the art and described in U.S. Application Pub. No. 2004/0219598A1.

The peptide can be used either by itself as an injectable immunogen, or incorporated into a non PTH peptide having a molecular weight, typically, of between about 5,000 and 10,000,000, or as part of the wPTH complete sequence. The PTH peptide may also be incorporated into a MAPS (Multiple Antigen Peptide System) by methods well known in the art. The immunogen can be mixed with an equal volume of Freund's complete adjuvant which is a mixture of light mineral oil, Arlacel A detergent, and inactivated mycobacterium tuberculosis bacilli. The resulting mixture is homogenized to produce an aqueous/oil emulsion which is injected into the animal (typically a goat) for the primary immunization. The immunogen dose can be approximately 50-400 micrograms. Mammals, such as goats can be injected monthly with the same dose of immunogen complex except no mycobacterium tuberculosis bacilli is used in subsequent injections. The animals can be bled monthly, approximately three months after the primary immunization. The serum (or antiserum) can be derived from each bleeding by separating the red blood cells from the blood by centrifugation and removing the antiserum which is rich in initial sequence PTH antibodies. Any other immunization methods with the PTH peptide may be used.

The antiserum for the desired PTH antibody can be purified by a combination of a positive adsorption to a PTH peptide having an amino acid sequence which starts at amino acid position 1 or 2 and ends at any amino acid position ranging from 4 to 84 of whole PTH, and a negative adsorption to a PTH peptide having an amino acid sequence which starts at any amino acid position ranging from 2 to 20 and ends at any amino acid position ranging from 6 to 84 of whole PTH, provided that each PTH peptide has a minimum length of at least 4 amino acids. The PTH peptide used for the negative adsorption is truncated at its N-terminal end by at least one amino acid more than is the PTH peptide used for the positive adsorption, thus the PTH peptide used for the negative adsorption lacks at least one N-terminal amino acid that is present in the PTH peptide used for the positive adsorption. In some embodiments, the purification step uses a combination of a positive adsorption to a PTH peptide having an amino acid sequence which starts at amino acid position 1 or 2 and ends at any amino acid position ranging from 4 to 84, or from 16 to 84, of whole PTH, and a negative adsorption to a PTH peptide having an amino acid sequence which starts at any amino acid position ranging from 2 to 20, or from 2 to 7, and ends at any amino acid position ranging from 6 to 84, or from 16 to 84, of whole PTH, provided that each PTH peptide has a minimum length of at least 4 amino acids. The positive adsorption and the negative adsorption may be performed in any order, with any combination of the peptides described, and either or both steps may be performed more than once.

For the positive adsorption, any affinity purification methods can be used, e.g., using a resin bound with the PTH peptide. A PTH peptide ranging from $PTH_{1-4}$ to $PTH_{1-84}$ (SEQ ID NO:1) can be used, e.g. $PTH_{1-4}$, $PTH_{1-5}$, $PTH_{1-6}$, $PTH_{1-7}$, $PTH_{1-8}$, $PTH_{1-9}$, $PTH_{1-10}$, $PTH_{1-11}$, $PTH_{1-12}$, $PTH_{1-13}$, $PTH_{1-14}$, $PTH_{1-15}$, $PTH_{1-16}$ to $PTH_{1-84}$ (e.g., $PTH_{1-16}$, $PTH_{1-17}$, $PTH_{1-18}$, $PTH_{1-19}$, $PTH_{1-20}$, $PTH_{1-21}$, $PTH_{1-22}$, $PTH_{1-23}$, $PTH_{1-24}$, $PTH_{1-25}$, $PTH_{1-26}$, $PTH_{1-27}$, $PTH_{1-28}$, $PTH_{1-29}$, $PTH_{1-30}$, $PTH_{1-31}$, $PTH_{1-32}$, $PTH_{1-33}$, $PTH_{1-34}$, $PTH_{1-35}$, $PTH_{1-36}$, $PTH_{1-37}$, $PTH_{1-38}$, $PTH_{1-39}$, $PTH_{1-40}$, $PTH_{1-41}$, $PTH_{1-42}$, $PTH_{1-43}$, $PTH_{1-44}$, $PTH_{1-45}$, $PTH_{1-46}$, $PTH_{1-47}$, $PTH_{1-48}$, $PTH_{1-49}$, $PTH_{1-50}$, $PTH_{1-51}$, $PTH_{1-52}$, $PTH_{1-53}$, $PTH_{1-54}$, $PTH_{1-55}$, $PTH_{1-56}$, $PTH_{1-57}$, $PTH_{1-58}$, $PTH_{1-59}$, $PTH_{1-60}$, $PTH_{1-61}$, $PTH_{1-62}$, $PTH_{1-63}$, $PTH_{1-64}$, $PTH_{1-65}$, $PTH_{1-66}$, $PTH_{1-67}$, $PTH_{1-68}$, $PTH_{1-69}$, $PTH_{1-70}$, $PTH_{1-71}$, $PTH_{1-72}$, $PTH_{1-73}$, $PTH_{1-74}$, $PTH_{1-75}$, $PTH_{1-76}$, $PTH_{1-77}$, $PTH_{1-78}$, $PTH_{1-79}$, $PTH_{1-80}$, $PTH_{1-81}$, $PTH_{1-82}$, $PTH_{1-83}$, and $PTH_{1-84}$) may be used. Or a peptide ranging from PTH2-5 to PTH 2-84 can be used, e.g. $PTH_{2-5}$ to $PTH_{2-6}$, $PTH_{2-7}$, $PTH_{2-8}$, $PTH_{2-9}$, $PTH_{2-10}$, $PTH_{2-11}$, $PTH_{2-12}$, $PTH_{2-13}$, $PTH_{2-14}$, $PTH_{2-15}$, $PTH_{2-16}$, $PTH_{2-17}$, $PTH_{2-18}$, $PTH_{2-19}$, $PTH_{2-20}$, $PTH_{2-21}$, $PTH_{2-22}$, $PTH_{2-23}$, $PTH_{2-24}$, $PTH_{2-25}$, $PTH_{2-26}$, $PTH_{2-27}$, $PTH_{2-28}$, $PTH_{2-29}$, $PTH_{2-30}$, $PTH_{2-31}$, $PTH_{2-32}$, $PTH_{2-33}$, $PTH_{2-34}$, $PTH_{2-35}$, $PTH_{2-36}$, $PTH_{2-37}$, $PTH_{2-38}$, $PTH_{2-39}$, $PTH_{2-40}$, $PTH_{2-41}$, $PTH_{2-42}$, $PTH_{2-43}$, $PTH_{2-44}$, $PTH_{2-45}$, $PTH_{2-46}$, $PTH_{2-47}$, $PTH_{2-48}$, $PTH_{2-49}$, $PTH_{2-50}$, $PTH_{2-51}$, $PTH_{2-52}$, $PTH_{2-53}$, $PTH_{2-54}$, $PTH_{2-55}$, $PTH_{2-56}$, $PTH_{2-57}$, $PTH_{2-58}$, $PTH_{2-59}$, $PTH_{2-60}$, $PTH_{2-61}$, $PTH_{2-62}$, $PTH_{2-63}$, $PTH_{2-64}$, $PTH_{2-65}$, $PTH_{2-66}$, $PTH_{2-67}$, $PTH_{2-68}$, $PTH_{2-69}$, $PTH_{2-70}$, $PTH_{2-71}$, $PTH_{2-72}$, $PTH_{2-73}$, $PTH_{2-74}$, $PTH_{2-75}$, $PTH_{2-76}$, $PTH_{2-77}$, $PTH_{2-78}$, $PTH_{2-79}$, $PTH_{2-80}$, $PTH_{2-81}$, $PTH_{2-82}$, $PTH_{2-83}$, and $PTH_{2-84}$ may be used.

For the negative adsorption, any purification method that removes at least one PTH peptide-binding antibody can be used, e.g. a resin bound with a PTH peptide such as PTH2-6 to PTH2-84, or PTH3-6 to PTH3-84, for example; provided that the PTH peptide used for the negative adsorption is missing at least one N-terminal amino acid that is present at the N-terminus of the PTH peptide used for the positive selection.

The PTH peptide bound resin may be made using methods known in the art. For example, PTH peptides may be immobilized to a gel, CNBr-activated Sepharose 4B from Pharmacia by coupling the Sepharose to primary amino groups of the PTH peptides. The gels with peptides immobilized may be packed into a column for antibody purification or used in a free gel form for negative adsorption. The PTH bound resin generated can be washed and packed into a column for affinity purification. The column may be equilibrated with a buffer (e.g., 0.01 M phosphate buffered saline (PBS)). The antiserum can then be loaded onto the column and washed with a buffer (e.g., 0.01 M PBS) in order to remove non-IgG serum protein and antibodies nonreactive to the immobilized PTH. The bound specific PTH polyclonal antibody may be eluted from the solid phase that includes optionally $PTH_{1-16}$ to $PTH_{1-84}$ in the column by passing an elution solution (e.g., 0.1 M glycine hydrochloride buffer, pH 2.5) through the column. The eluted polyclonal antibody may further be neutralized after it leaves the column, for example, with either the addition of 1.0 M phosphate buffer, pH 7.5 or by a buffer exchange with 0.01 M PBS, as is known to those of skill in the art.

The antibody is also purified by negative adsorption to a PTH peptide having an amino acid sequence which starts at any amino acid position ranging from 2 to 20, often from 2 to 7, and ends at any amino acid position ranging from 6 to 84, often from 16 to 84, of the whole PTH; provided that the PTH peptide used for the negative adsorption lacks at least one N-terminal amino acid that is present in the PTH peptide used for the positive adsorption. In some embodiments, the PTH peptide used for the negative adsorption starts one amino acid later in the PTH sequence than does the PTH peptide used for the positive adsorption. In some embodiments, the PTH peptide used for the negative adsorption ends with the same amino acid position as the PTH peptide used for the positive adsorption described above. For example, the PTH peptide used for negative adsorption may be $PTH_{2-16}$, $PTH_{3-16}$, $PTH_{4-16}$, $PTH_{5-16}$, $PTH_{6-16}$, $PTH_{7-16}$, $PTH_{2-34}$, $PTH_{3-34}$, $PTH_{4-34}$, $PTH_{5-34}$, $PTH_{6-34}$, $PTH_{7-34}$, $PTH_{2-84}$, $PTH_{3-84}$, $PTH_{4-84}$, $PTH_{5-84}$, $PTH_{6-84}$, $PTH_{7-84}$. The negative adsorption may be performed using a PTH peptide bound resin. The PTH peptide can be bound to a resin (such as a bead or a gel) using any methods known in the art or methods described herein. The antibody may be incubated with the PTH peptide resin for negative adsorption. The incubation may be carried out at room temperature or at 2-8° C. for 2 hours to overnight. The polyclonal antibody collected after the negative adsorption can be stored at 2-8° C. or frozen.

One of skill in the art would understand that there are acceptable variations in the above practices. See, e.g., Harlow E, Lane D: ANTIBODIES: A LABORATORY MANUAL. (Cold Spring Harbor Laboratory Press, Cold Spring Harbor, N.Y., 1988); Kohler & Milstein, *Nature*, 256: 495-7 (1975).

The invention also provides isolated anti-PTH antibodies produced by the methods of the invention. The epitope that the anti-PTH antibody binds to may be a linear epitope or a conformational epitope. These anti-PTH antibodies may bind to an epitope which includes one or more of the first six N-terminal amino acids of a whole PTH. In some embodiments, the antibody specifically binds to an epitope which includes the first and/or the second N-terminal amino acids of the whole PTH.

In some embodiments, the isolated anti-PTH antibody binds to the PTH peptide used as the immunogen with higher affinity than the isolated anti-PTH antibody binds to any of the PTH peptides contained within the PTH peptide immunogen. In some embodiments, the binding affinity is at least about 10%, at least about 20%, at least about 30%, at least about 50%, at least about 60%, at least about 70%, at least about 80%, or at least about 90% higher than, or at least about two-fold, at least about five-fold, at least about ten-fold, or more of the binding affinity compared to. For example, the isolated anti-PTH antibody may bind to $PTH_{1-84}$ (SEQ ID NO:1) with higher affinity than any of $PTH_{1-5}$, $PTH_{1-6}$, $PTH_{1-7}$, $PTH_{1-8}$, $PTH_{1-9}$, $PTH_{1-10}$, $PTH_{1-12}$, $PTH_{1-15}$, $PTH_{2-12}$, and $PTH_{2-15}$.

In some embodiments, the isolated anti-PTH antibody does not specifically binds to a PTH peptide selected from the group consisting of $PTH_{1-5}$, $PTH_{1-6}$, $PTH_{1-7}$, $PTH_{1-8}$, $PTH_{1-9}$, $PTH_{1-10}$, $PTH_{1-12}$, $PTH_{1-15}$, $PTH_{2-12}$, and $PTH_{2-15}$. The term "does not specifically bind to" means that the isolated anti-PTH antibody binds to the PTH peptide used as the immunogen with higher affinity than the isolated anti-PTH antibody binds to any of $PTH_{1-5}$, $PTH_{1-6}$, $PTH_{1-7}$, $PTH_{1-8}$, $PTH_{1-9}$, $PTH_{1-10}$, $PTH_{1-12}$, $PTH_{1-15}$, $PTH_{2-12}$, or $PTH_{2-15}$. In some embodiments, the binding affinity is at least about 10%, at least about 20%, at least about 30%, at least about 50%, at least about 60%, at least about 70%, at least about 80%, or at least about 90% higher than, or at least about two-fold, at least about five-fold, at least about ten-fold or more of the binding affinity compared to.

In some embodiments, the antibody is capable of detecting the whole PTH at a physiological level in a mammalian sample.

In some embodiments, the antibody avoids binding to a non-whole PTH fragment. In some embodiments, the non-whole PTH fragment is a peptide having an amino acid sequence from between $PTH_{3-84}$ and $PTH_{34-84}$ (e.g., $PTH_{7-84}$).

In some embodiments, the antibody is a monoclonal or a polyclonal antibody, or antibody fragment. In some embodiments, the antibody specifically binds to human PTH.

C. Methods of Using Anti-PTH Antibodies that Specifically Bind to an Epitope that Includes N-terminal Amino Acids of a Whole PTH The antibodies of the invention may be used in any PTH immunoassays.

The invention provides a method for measuring whole parathyroid hormone (PTH) in a mammalian sample, which method comprises: a) obtaining a sample from a mammal to be tested; b) contacting said sample with the isolated antibody generated by the methods described herein; and c) assessing a complex formed between said whole parathyroid hormone, if present in said sample, and said antibody, to measure the level of said whole parathyroid hormone in said mammalian sample.

These methods may be used for measuring wPTH in any biological samples, for example, blood, plasma or serum. The sample may be a clinical sample. The sample may be from a human. Physiological levels of wPTH in a mammalian sample may be detected. In some embodiments, the level of wPTH measured in the sample is less than about 4 pmol/L. In other embodiments, the level of wPTH measured is from about 0.2 pmol/L to about 4 pmol/L. In some embodiments, the level of wPTH measured is from is between about 2 pgm/ml to about 40 pgm/ml. In some embodiments, the level of wPTH measured is from is between about 7 pgm/ml to about 39 pgm/ml.

Although a variety of assay types are contemplated, the present methods frequently assess the complex formed between the whole parathyroid hormone and the antibody via a sandwich or competitive assay format. In some embodiments, the complex is assessed in a homogeneous or a heterogeneous assay format. In some embodiments, the complex is assessed by a format selected from the group consisting of an enzyme-linked immunosorbent assay (ELISA), chemiluminescent assay, immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, plasmon resonance assay, chemiluminescence assay, lateral flow immunoassay, u-capture assay, inhibition assay and avidity assay.

In some embodiments, the whole PTH in a sample is measured using a sandwich assay. See, e.g., U.S. Pat. Nos. 6,743,590; 6,689,566; and U.S. Pub. No. 2004/0219598A1. In the sandwich assay, the antibody generated according to the methods of the invention may be used as the first antibody, and another antibody that is capable of binding to an epitope on the wPTH other than the epitope which the antibody generated according to the methods of the invention binds to is used as a second antibody. Either the first or second antibody may be attached to a surface and functions as a capture antibody. The capture antibody may be attached to the surface directly or indirectly. Methods of attaching antibody to a surface are known in the art. For example, the capture antibody may be attached to the surface via a biotin-avidin (or streptavidin) linking pair. Capture antibody coated tubes or beads can be created by attaching affinity purified goat anti PTH 39-84 antibody, (Scantibodies Laboratory, Inc., Santee, Calif., U.S.A.), to polystyrene tubes (e.g., 12×75 mm tubes from Nunc, Denmark) or polystyrene beads (e.g., 6 or 8 mm beads from Hoover, Inc., MI, USA) by means of passive absorption techniques which are known to those of skill in the art. The tubes are emptied and dried, creating solid phase antibody coated tubes.

Either the first or the second antibody may be labeled and used as the signal antibody or tracer antibody. The signal antibody may be linked to any detectable labels, such as radioisotopes, chemiluminescence, enzyme, fluorescence, particulate labels (e.g., colloidal particles or latex particles) using any techniques known in the art.

In an exemplary embodiment, an immunoradiometric assay (IRMA) is used. Elements employed in such an assay include a capture antibody attached to a solid support and a signal antibody having a label, attached thereto. Typically, one selects a capture antibody that is specific for C-terminal PTH fragments, while the labeled antibody is the anti-PTH antibody generated according to the methods described herein which specifically binds to an epitope which includes one or more N-terminal amino acid residues of a wPTH.

Alternatively, one could create an immunoassay in which wPTH is either precipitated from solution or otherwise differentiated in a solution, as in conventional precipitating assays or turbidometric assays. For example, one can use at least three antibodies to form a precipitating mass. In addition to the anti-PTH antibody generated according to the methods of the invention and a C-terminal antibody, one can use at least a third antibody which attaches to the mid portion of PTH. The combined mass of wPTH and the at least three antibodies would form a labeled precipitating mass which can be measured by conventional techniques.

The present methods may be utilized to measure multiple PTH peptide components, such as a non-whole PTH peptide fragment level and/or a total PTH level, in addition to a whole PTH level. In such embodiments, the methods frequently further comprise comparing at least two parameters selected from the group consisting of the whole PTH level (wPTH), total PTH level, total PTH peptide fragment level, C-terminal PTH fragment level (cPTH), N-terminal PTH fragment level, and mid-terminal PTH fragment level (mPTH). The comparison of parameters is generally in the form of a ratio or proportion. Frequently, the results of said comparison are used to determine whether the mammal, often a human patient, is afflicted with a bone turnover related disorder, or used to monitor bone disease related treatment. Also frequently, the present methods are used to determine or diagnose whether the mammal is afflicted with, or at risk of, adynamic bone disease or severe hyperparathyroidism. Frequently, the present methods are used for clinical management of renal disease subjects and subjects afflicted with osteoporosis, including dialysis patients. Also frequently, the present methods are used for diagnosing primary hyperparathyroidism. Moreover, the present methods are useful for clinical diagnosis and management of subjects having adynamic bone disease induced, in part, through the practice of inappropriate treatment protocols.

The comparison may take many forms. For example, the comparison can be in the form of a ratio or proportion between the whole PTH level versus the total PTH level (i.e., represented by the equation: wPTH/total PTH); between the whole PTH level versus the combined cPTH and mPTH fragment levels (i.e., represented by the equation: wPTH/(cPTH+mPTH)); between the whole PTH level versus the combined cPTH and mPTH fragment levels, wherein double the whole PTH level is subtracted from the combined cPTH and mPTH fragment levels (i.e., represented by the equation: wPTH/((cPTH−wPTH)+(mPTH−wPTH))); between the whole PTH level versus the total of the combined cPTH and mPTH fragment levels subtracted by the whole PTH level (i.e., represented by the equation: wPTH/(cPTH+mPTH−wPTH)); between the whole PTH level versus the combined whole PTH level, cPTH and mPTH fragment levels (i.e., represented by the equation: wPTH/(wPTH+cPTH+mPTH)); between the whole PTH level versus the cPTH fragment level (i.e., represented by the equation: wPTH/cPTH); between the whole PTH level versus the mPTH fragment level (i.e., represented by the equation: wPTH/mPTH); between the whole PTH level versus the total PTH level minus the whole PTH level (i.e., represented by the equation: wPTH/(total PTH−wPTH)); or other combinations of the disclosed parameters, including, without limitation, the inverse of each comparison. Moreover, the log of any of the above mentioned ratios or comparisons, or the negative log thereof, may be used. Moreover, without limitation, in one aspect, the value obtained from determining the total PTH level and subtracting this level from the whole PTH level yields the total PTH fragment level in a sample/subject. The cutoff ranges for each of these comparisons as they are associated with a particular bone turnover, treatment, disease or disorder vary as provided herein (see e.g., Table 2 and accompanying discussion).

Frequently in the present methods the sample is contacted with one or more isolated antibodies, and wherein each of said one or more isolated antibodies specifically binds one or more PTH peptide fragments selected from the group consisting of: $PTH_{39-84}$, $PTH_{1-34}$, $PTH_{43-68}$, $PTH_{7-84}$, $PTH_{39-68}$, $PTH_{53-84}$, $PTH_{65-84}$, $PTH_{44-68}$, $PTH_{19-84}$, $PTH_{23-84}$, $PTH_{1-38}$, $PTH_{1-48}$, $PTH_{1-58}$, $PTH_{1-68}$ and $PTH_{1-78}$.

The present methods of measuring multiple PTH components provide a variety of uses. For example, such methods are used for differentiating between a person having substantially normal parathyroid function and having hyperparathyroidism, e.g., primary hyperparathyroidism; monitoring parathyroid related bone disease and treatment; monitoring effects of therapeutic treatment for hyperparathyroidism; diagnosing parathyroid related bone disease; clinical management of renal disease subjects and renal disease related treatments and subjects afflicted with osteoporosis and osteoporosis related treatments.

Kits

The invention also provides kits for use in the instant methods. In one aspect, the invention provides kits for producing an antibody to a PTH peptide, which kits comprise: a) an isolated PTH peptide having an amino acid sequence which starts at amino acid position 1 and ends at any amino acid position ranging from 34 to 84 of a whole PTH; b) means for introducing said isolated PTH peptide to a mammal in an amount sufficient to produce an antibody to said PTH peptide; c) a resin coupled with a PTH peptide having an amino acid sequence which starts at amino acid position 1 or 2 and ends at any amino acid position ranging from 4 to 84, or from 16 to 84, of said whole PTH; and d) a resin coupled with a PTH peptide having an amino acid sequence which starts at any amino acid position ranging from 2 to 20, or from 2 to 7, and ends at any amino acid position ranging from 6 to 84, or from 16 to 84, of the whole PTH, provided the peptide is at least four amino acids in length, and the PTH peptide used for the negative adsorption lacks at least one N-terminal amino acid that is present in the PTH peptide used for the positive adsorption. In some embodiments, the PTH peptide in d) ends at the same amino acid position as the PTH peptide in c). The means for introducing a PTH peptide to a mammal to produce an antibody are known in the art, for example, an adjuvant and a syringe for injection. In some embodiments, the kits further provide instructions for using the resin in c) for affinity purification of the PTH antibody and using the resin in d) for further purification of the PTH antibody by negative absorption.

The present invention also provides kits for measuring the level of PTH in a mammalian sample, which kits comprise an anti-PTH antibody described herein. In some embodiments, the kits are used for measuring a physiological level of whole PTH in a mammalian sample. In some embodiments, the kits may further comprise a second PTH antibody for performing a sandwich assay. The kits may further comprise instructions for performing sandwich radioimmunoassay described herein.

The kits of the invention are in suitable packaging. Suitable packaging includes, but is not limited to, vials, bottles, jars, flexible packaging (e.g., plastic bags), and the like. Kits may optionally provide additional components such as buffers and interpretive information. Normally, the kits comprise a container and a label or package insert(s) on or associated with the container.

EXAMPLES

Example 1

Preparation of Anti-PTH Antibodies that Specifically Bind to an Epitope that Includes the First N-terminal Amino Acid of Human Whole PTH Human whole $PTH_{1-84}$ was used as immunogen for injection into a goat. The immunogen was mixed with an equal volume of Freund's complete adjuvant which is a mixture of light mineral oil, Arlacel A detergent, and inactivated *Mycobacterium tuberculosis* bacilli. The resulting mixture was homogenized to produce an aqueous/oil emulsion which was injected into the goats for the primary immunization. The immunogen dose was approximately 50-400 micrograms. The goats were injected monthly with the same dose of immunogen complex except no *Mycobacterium tuberculosis* bacilli was used in these subsequent injections. The goats were bled monthly, approximately three months after the 20 primary immunizations. The serum (or antiserum) was derived from each bleeding by separating the red blood cells from the blood by centrifugation and removing the antiserum which was rich in PTH antibodies.

To affinity purify the antiserum for the desired whole PTH antibody that are specific for the N-terminal amino acids, a separation column with $PTH_{1-34}$ bound gels was prepared. The gels were prepared by reacting CNBr-activated Sepharose 4B from Pharmacia to the primary amino groups of the $PTH_{1-34}$ according to the manufacturer's instructions. The column was washed and equilibrated with 0.01 M phosphate buffered saline (PBS). The antiserum was loaded onto the column and washed with 0.01 M PBS. The antibody bound to the column was eluted from the solid phase by passing an elution solution of 0.1 M glycine hydrochloride buffer, pH 2.5, through the column. The pH of the eluted antibody solution was neutralized with the addition of either 1.0 M phosphate buffer, pH 7.5, or by a buffer exchange with 0.01 M PBS.

The eluted antibodies from the affinity purification were further purified by negative adsorption with a gel coupled to $PTH_{2-34}$ so that $PTH_{2-34}$ was immobilized. The gel coupled to $PTH_{2-34}$ was prepared as described above. The eluted antibodies were incubated with the $PTH_{2-34}$ bound gel at room temperature for 2 hours, 3.5 hours, 4 hours or overnight at 2-8° C. The antibodies that were not bound to the gel after the incubation were eluted through a column with a gel supporting filter using 0.01 M PBS as the elution buffer and the eluted antibody was collected for use as the tracer antibody in the whole PTH assay described below. These antibodies were named PTH-plus antibodies (alternatively referred to as "PTH(1-34) CAP antibody" or "1-34 CAP Ab" in the following examples).

Example 2

Whole PTH IRMA Assays Using PTH-Plus Antibodies

The anti-PTH antibody (PTH-plus antibody) generated in Example 1 was used as the tracer antibody in a whole PTH immunoradiometric assay (IRMA), often referred to as a sandwich assay (Scantibodies Laboratories, Santee, Calif., USA). The assay used a goat polyclonal antibody that recognizes $PTH_{1-84}$ the 39-84 region of the PTH molecule as the capture antibody which was attached to the surface of polystyrene-coated beads or tubes. The PTH-plus antibody or anti-PTH antibody that recognizes human $PTH_{1-84}$ in the N-terminal $PTH_{1-9}$ region was used as the signal antibody. The signal antibody was labeled with $^{125}I$ by oxidation with chloramine T, incubation for 25 seconds at room temperature with 1 millicurie of $^{125}I$ radioisotope, and followed by reduction with sodium metabisulfate. Unincorporated $^{125}I$ radioisotope was separated from the labeled signal antibody by passing the iodination mixture over a PD-10 desalting column (Pharmacia, Uppsala, Sweden) and following the manufactures instructions. The fractions collected from the PD-10 desalting column were measured in a gamma counter, and those fractions representing the $^{125}I$-goat anti-PTH antibodies were pooled and diluted to approximately 300,000 D PM (disintegrations per minute) per 100 microliters. This solution was used as the tracer solution in the whole PTH assay.

Whole PTH IRMA assay data using the PTH-plus antibody as the tracer antibody generated according to the method in Example 1 was compared to the IRMA assay that used the anti-PTH antibody directed to N-terminal PTH peptides (tracer antibody that bound the $PTH_{1-84}$ in the $PTH_{1-9}$ region). To conduct a whole PTH assay of a sample, 200 microliter samples of human EDTA plasma were added to the solid phase antibody coated tubes or beads. To each tube was added 100 microliters of the tracer solution (labeled goat anti-(1-9) PTH or $PTH_{1-34}$ CAP antibody). The tubes were incubated at room temperature with shaking at 170 rpm for 20-22 hours. During this time the immunochemical reaction of forming the sandwich of {solid phase goat anti-(39-84) PTH antibody}-{whole PTH}-{$^{125}I$-goat anti-(1-9) PTH antibody} or {$^{125}I$-goat $PTH_{1-34}$ CAP antibody) took place. Following this incubation, the test tubes or beads were washed with wash buffer (Phosphate buffered saline (PBS) containing 0.1% Triton X-100 and 0.05% sodium azide). Radioactivity on the solid phase, which amount corresponded to the quantity of wPTH present, was measured using a gamma counter. The radioactivity data for the samples was processed by conventional analysis with use of the results from standards and controls and computer software in order that the concentration of whole PTH in the samples was ascertained.

Table 1 below shows the comparison of $PTH_{1-34}$ CAP antibodies generated by immunization with $PTH_{1-34}$, affinity purified on a $PTH_{1-34}$ peptide column, and further purified by negative adsorption with solid phase supported $PTH_{2-34}$ at room temperature for 3.5 hours. Plasma samples from 40 dialysis patients were tested side-by-side in the two assays that used both antibodies.

TABLE 1

Comparison of using $PTH_{1-34}$ CAP antibody and anti-($PTH_{1-9}$) antibody in wPTH determination in patient plasma.

| | CAP PTH (pg/ml) | | |
|---|---|---|---|
| Patients | Control 1-9 Ab | $PTH_{1-34}$ CAP | Ratio $PTH_{1-34}$ CAP/1-9 |
| 1. | 1329.8 | 1154.6 | 86.8% |
| 2. | 24.69 | 22.56 | 91.4% |
| 3. | 17.21 | 17.36 | 100.9% |
| 4. | 386.95 | 388.41 | 100.4% |
| 5. | 174.39 | 190.29 | 109.1% |
| 6. | 28.75 | 26.8 | 93.2% |

TABLE 1-continued

Comparison of using $PTH_{1-34}$ CAP antibody and anti-$(PTH_{1-9})$ antibody in wPTH determination in patient plasma.

| Patients | CAP PTH (pg/ml) | | Ratio $PTH_{1-34}$ CAP/1-9 |
|---|---|---|---|
| | Control 1-9 Ab | $PTH_{1-34}$ CAP | |
| 7. | 143.94 | 143.7 | 99.8% |
| 8. | 55.84 | 58.72 | 105.2% |
| 9. | 143.17 | 135.8 | 94.9% |
| 10. | 362.11 | 346.42 | 95.7% |
| 11. | 467.57 | 450.57 | 96.4% |
| 12. | 44.21 | 46.9 | 106.1% |
| 13. | 35.04 | 34.67 | 98.9% |
| 14. | 592.72 | 625.57 | 105.5% |
| 15. | 535.47 | 523.13 | 97.7% |
| 16. | 144.45 | 139.07 | 96.3% |
| 17. | 503 | 594.51 | 118.2% |
| 18. | 26.35 | 26.78 | 101.6% |
| 19. | 11.14 | 19.61 | 176.0% |
| 20. | 198.79 | 231.74 | 116.6% |
| 21. | 11.72 | 11.5 | 98.1% |
| 22. | 35.12 | 35.62 | 101.4% |
| 23. | 345.71 | 380.35 | 110.0% |
| 24. | 211.54 | 229.2 | 108.3% |
| 25. | 140.36 | 136.83 | 97.5% |
| 26. | 477.05 | 598.05 | 125.4% |
| 27. | 204.48 | 199.26 | 97.4% |
| 28. | 235.81 | 236.25 | 100.2% |
| 29. | 336.97 | 364.03 | 108.0% |
| 30. | 146.55 | 142.25 | 97.1% |
| 31. | 201.77 | 214.08 | 106.1% |
| 32. | 260.38 | 308.34 | 118.4% |
| 33. | 287.56 | 263.68 | 91.7% |
| 34. | 505.39 | 528.7 | 104.6% |
| 35. | 522.8 | 529.68 | 101.3% |
| 36. | 226.99 | 234.06 | 103.1% |
| 37. | 213.63 | 291.62 | 136.5% |
| 38. | 387.55 | 368.36 | 95.0% |
| 39. | 33.72 | 37.38 | 110.9% |
| 40. | 107.37 | 108 | 100.6% |
| Avg | 252.95 | 259.86 | 105.1% |

As shown in FIG. 1, linear regression statistical analysis of the resulting data led to an equation: y=0.9432x+21.277; $R^2$=0.9723 where y=mx+b. The significant correlation ($R^2>0.9$) and the tight slope (0.9-1.1) suggested statistical equivalency in performance with the two assays that used these two antibodies.

Table 2 below shows the comparison of PTH-plus antibodies (AB1 and AB2) generated by immunization with $PTH_{1-84}$ (SEQ ID NO:1) and affinity purified on a $PTH_{1-34}$ peptide column, and further purified by negative adsorption for 2 hours (AB1) at room temperature on a rotator or overnight at 2-8° C. (AB2) with $PTH_{2-34}$ peptide gel. Negative adsorption for the AB2 antibody includes one change of the $PTH_{2-34}$ gel. Antibody recovery was 22% for AB1 and 18.8% for AB2. Plasma samples from 40 dialysis patients were tested side-by-side for anti-$PTH_{1-9}$ antibody (G659D), and PTH-plus antibodies AB1 and AB2.

TABLE 2

Comparison of using PTH-plus antibody and anti-PTH1-9 antibody in wPTH determination in patient plasma.

| Patient Acces# | CAP (pg/ml) | | | Ratio | | |
|---|---|---|---|---|---|---|
| | Control 1-9 Ab tracer | AB1 tracer (2 hrs. N.A.) | AB2 tracer (O/N.N.A.) | AB1/ctrl % | AB2/ctrl % | AB2/AB1 % |
| B047167 | 240.3 | 245.56 | 221.43 | 102.2% | 92.1% | 90.2% |
| B047462 | 329.89 | 309.55 | 292.84 | 93.8% | 88.8% | 94.6% |
| B047168 | 184.18 | 182.92 | 176.12 | 99.3% | 95.6% | 96.3% |
| B047166 | 122.37 | 89.67 | 81.45 | 73.3% | 66.6% | 90.8% |
| B047456 | 237.09 | 198.15 | 191.96 | 83.6% | 81.0% | 96.9% |
| B047475 | 263.47 | 253.07 | 212.46 | 96.1% | 80.6% | 84.0% |
| B047169 | 143.9 | 162.03 | 143.96 | 112.6% | 100.0% | 88.8% |
| B047556 | 93.16 | 95.96 | 92.68 | 103.0% | 99.5% | 96.6% |
| B047443 | 105.51 | 98.81 | 89.85 | 93.6% | 85.2% | 90.9% |
| B047158 | 112.57 | 124.58 | 87.69 | 110.7% | 77.9% | 70.4% |
| B047421 | 17.13 | 18.45 | 15.9 | 107.7% | 92.8% | 86.2% |
| B047171 | 184.52 | 199.62 | 180.53 | 108.2% | 97.8% | 90.4% |
| B047417 | 307.62 | 316.89 | 272.56 | 103.0% | 88.6% | 86.0% |
| B047536 | 208.55 | 193.06 | 158.73 | 92.6% | 76.1% | 82.2% |
| B047560 | 178.37 | 189.81 | 163.85 | 106.4% | 91.9% | 86.3% |
| B047498 | 88.82 | 88.64 | 85.13 | 99.8% | 95.8% | 96.0% |
| B047569 | 144.91 | 140.61 | 127.28 | 97.0% | 87.8% | 90.5% |
| B047174 | 478.66 | 479.9 | 431.36 | 100.3% | 90.1% | 89.9% |
| B047164 | 259.57 | 224.49 | 197.17 | 86.5% | 76.0% | 87.8% |
| B047159 | 392.11 | 387.9 | 333.62 | 98.9% | 85.1% | 86.0% |
| B047561 | 274.18 | 252.87 | 218.73 | 92.2% | 79.8% | 86.5% |
| B047479 | 161.83 | 161.8 | 145.62 | 100.0% | 90.0% | 90.0% |
| B047562 | 402.7 | 401.93 | 365.84 | 99.8% | 90.8% | 91.0% |
| B047555 | 344.4 | 370.58 | 340.66 | 107.6% | 98.9% | 91.9% |
| B047429 | 40.2 | 42.4 | 39.16 | 105.5% | 97.4% | 92.4% |
| B047176 | 252.83 | 190.57 | 171.58 | 75.4% | 67.9% | 90.0% |
| B047557 | 26.07 | 24.66 | 20.24 | 94.6% | 77.6% | 82.1% |
| B047480 | 430.3 | 437.33 | 382.8 | 101.6% | 89.0% | 87.5% |
| B047458 | 35.65 | 39.19 | 34.65 | 109.9% | 97.2% | 88.4% |

TABLE 2-continued

Comparison of using PTH-plus antibody and anti-PTH1-9 antibody in wPTH determination in patient plasma.

| Patient Acces# | CAP (pg/ml) | | | Ratio | | |
|---|---|---|---|---|---|---|
| | Control 1-9 Ab tracer | AB1 tracer (2 hrs. N.A.) | AB2 tracer (O/N.N.A.) | AB1/ctrl % | AB2/ctrl % | AB2/AB1 % |
| B047160 | 64 | 67.02 | 59.69 | 104.7% | 93.3% | 89.1% |
| B047559 | 277.82 | 278.99 | 250.96 | 100.4% | 90.3% | 90.0% |
| B047558 | 26.62 | 21.07 | 24.8 | 79.2% | 93.2% | 117.7% |
| B047157 | 892.88 | 855.73 | 769.81 | 95.8% | 86.2% | 90.0% |
| B047538 | 1004.8 | 1098.7 | 1257.1 | 109.3% | 125.1% | 114.4% |
| B047564 | 232.11 | 208.15 | 187.28 | 89.7% | 80.7% | 90.0% |
| B047570 | 412.85 | 397.72 | 324.74 | 96.3% | 78.7% | 81.7% |
| B047156 | 310.34 | 303.79 | 305.36 | 97.9% | 98.4% | 100.5% |
| B047163 | 254.89 | 281.07 | 264.02 | 110.3% | 103.6% | 93.9% |
| B047566 | 145.52 | 155.63 | 159.99 | 106.9% | 109.9% | 102.8% |
| B047434 | 59.95 | 58.3 | 68.55 | 97.2% | 114.3% | 117.6% |
| Mean | 243.57 | 241.18 | 223.70 | 98.6% | 90.3% | 91.7% |
| R | | 0.99395 | 0.97116 | | | |
| Slope | | 1.0274 | 1.0426 | | | |

Figure 2A:
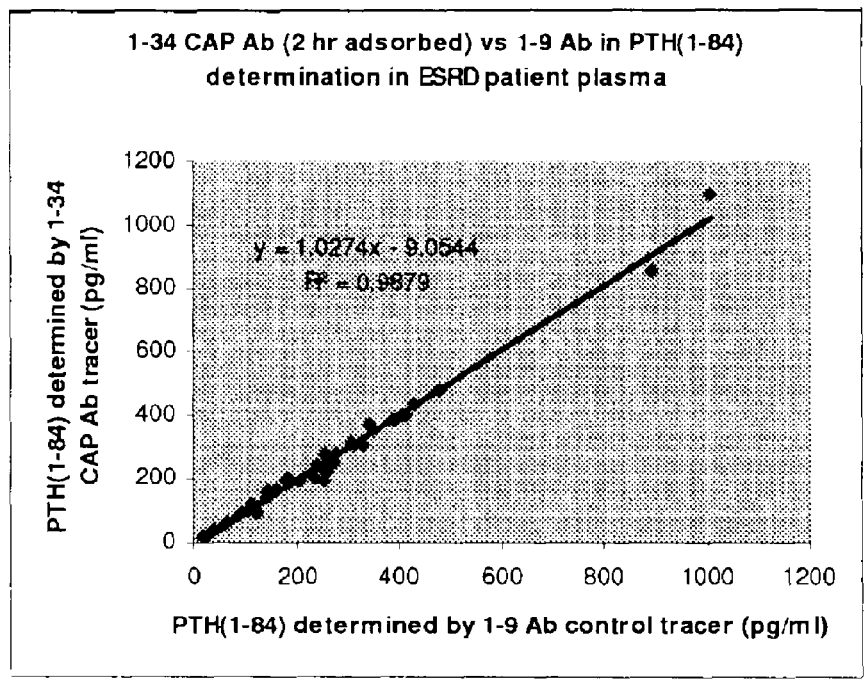
FIG. 2 is a graph showing the correlations a) between $PTH_{1-9}$ using the $PTH_{1-34}$ CAP antibody (negatively adsorbed with $PTH_{2-34}$ at room temperature for 2 hours in the manner described above) and the anti-$PTH_{1-9}$ antibody as defined above; b) between using the $PTH_{1-34}$ CAP antibody (negatively adsorbed with $PTH_{2-34}$ at 2-8° C. overnight) and the anti-$PTH_{1-9}$ antibody; c) between using the $PTH_{1-34}$ CAP antibody (negatively adsorbed with $PTH_{2-34}$ at room temperature for 2 hours) and the $PTH_{1-34}$ CAP antibody (negatively adsorbed with $PTH_{2-34}$ at 2-8° C. overnight) as tracer for wPTH determinations in patient plasma. Linear regression statistical analysis of the resulting data leads to the following equations: $y=1.0274x-9.0544$, $R^2=0.9879$ where $y=mx+b$ for (2A); $y=1.0426x-30.229$, $R^2=0.9432$ for (2B); and $y=1.0253x-23.576$, $R^2=0.9748$ for (2C).
Figure 2B:
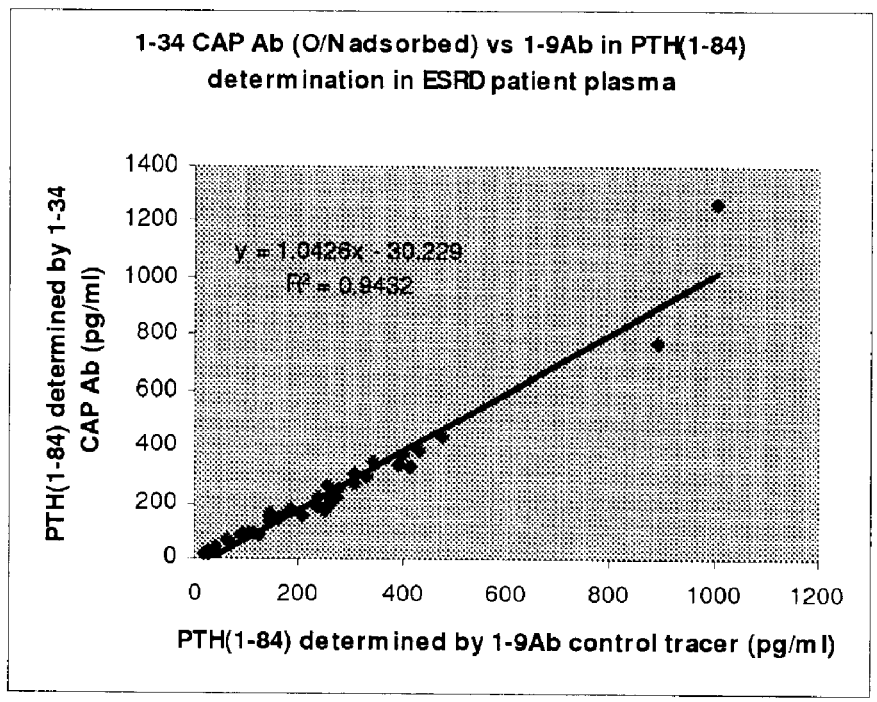
Figure 2C:
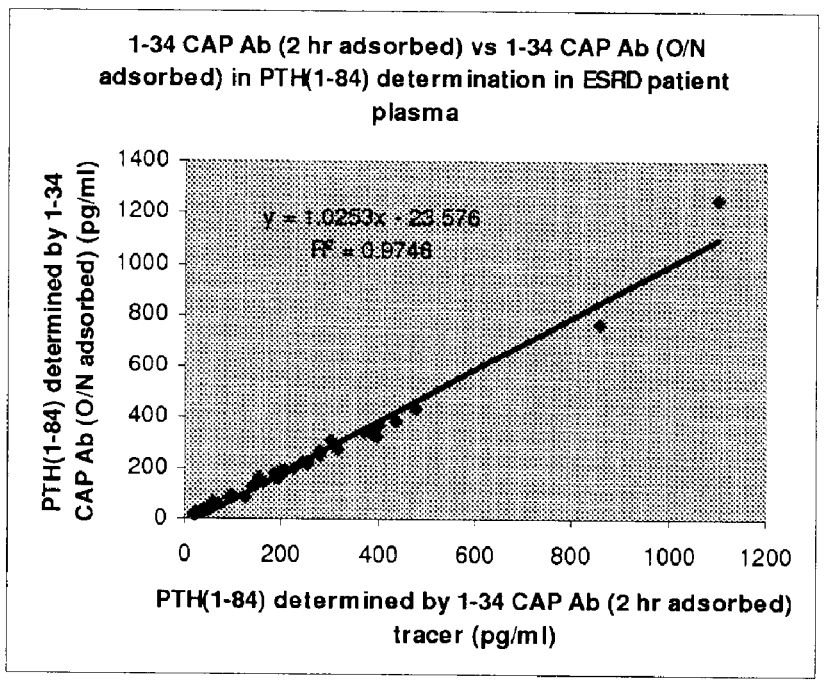

As shown in FIG. 2, the significant correlations ($R^2>0.9$) and the tight slopes (0.9-1.1) centered around a slope of 1.0 (which indicates equivalence) suggested statistical equivalence of the three antibodies ($PTH_{1-34}$ CAP antibody negatively adsorbed at room temperature for 2 hours, $PTH_{1-34}$ CAP antibody negatively adsorbed at 2-8° C. overnight, and anti-$PTH_{1-9}$ antibody control).

Table 3 below shows the comparison of another $PTH_{1-34}$ CAP antibody (lot G645D) generated by immunization with $PTH_{1-84}$ (SEQ ID NO:1), affinity purified on a $PTH_{1-34}$ peptide column, and further purified by negative adsorption overnight at 2-8° C. to a $PTH_{2-34}$ peptide gel. Plasma samples from 40 ESRD patients were tested side-by-side for anti-$PTH_{1-9}$ antibody and $PTH_{1-34}$ CAP antibody.

TABLE 3

Comparison of using $PTH_{1-34}$ CAP antibody and anti-$PTH_{1-9}$ antibody in wPTH determination in patient plasma.

| | Patient ID | Control (anti-PTH1-9 antibody) | $PTH_{1-34}$ CAP antibody | $PTH_{1-34}$ CAP antibody/ control % |
|---|---|---|---|---|
| 1 | 62026 | 149.55 | 147.28 | 98.48% |
| 2 | 62013 | 121.53 | 131.57 | 108.26% |
| 3 | 61890 | 176.37 | 172.91 | 98.04% |
| 4 | 61813 | 114.32 | 129.42 | 113.21% |
| 5 | 62027 | 126.29 | 125.07 | 99.03% |
| 6 | 61824 | 281.95 | 252.07 | 89.40% |
| 7 | 62052 | 290.27 | 273.15 | 94.10% |
| 8 | 61996 | 53.51 | 51.38 | 96.02% |
| 9 | 61907 | 178.81 | 203.35 | 113.72% |
| 10 | 61809 | 221.53 | 213.18 | 96.23% |
| 11 | 61999 | 150.03 | 145.14 | 96.74% |
| 12 | 62050 | 112.28 | 109.08 | 97.15% |
| 13 | 62041 | 318.35 | 311.28 | 97.78% |
| 14 | 61648 | 132.58 | 143.54 | 108.27% |
| 15 | 62075 | 31.42 | 35.39 | 112.64% |
| 16 | 61952 | 158.29 | 162.85 | 102.88% |
| 17 | 62031 | 228.96 | 224.63 | 98.11 |
| 18 | 62028 | 303.66 | 306.23 | 100.85% |
| 19 | 62040 | 367.59 | 362.97 | 98.74% |
| 20 | 62025 | 168.01 | 157.28 | 93.61% |
| 21 | 62064 | 107.06 | 109.7 | 102.47% |
| 22 | 62062 | 361.85 | 360.69 | 99.68% |
| 23 | 61900 | 550.39 | 516.73 | 93.88% |
| 24 | 61865 | 241.05 | 227.13 | 94.23% |
| 25 | 61878 | 228.12 | 203.64 | 89.27% |
| 26 | 62057 | 201.45 | 188.86 | 93.75% |

TABLE 3-continued

Comparison of using $PTH_{1-34}$ CAP antibody and anti-$PTH_{1-9}$ antibody in wPTH determination in patient plasma.

| | Patient ID | Control (anti-PTH1-9 antibody) | $PTH_{1-34}$ CAP antibody | $PTH_{1-34}$ CAP antibody/ control % |
|---|---|---|---|---|
| 27 | 61997 | 75.88 | 89.29 | 117.67% |
| 28 | 61948 | 82.28 | 85.59 | 104.02% |
| 29 | 62036 | 130.38 | 139.11 | 106.70% |
| 30 | 61945 | 52.57 | 61.2 | 116.42% |
| 31 | 61899 | 66.56 | 71.11 | 106.84% |
| 32 | 61931 | 178.66 | 185.47 | 103.81% |
| 33 | 62038 | 263.5 | 307.84 | 116.83% |
| 34 | 61889 | 265.98 | 257.69 | 96.88% |
| 35 | 61943 | 278.49 | 250.65 | 90.00% |
| 36 | 61901 | 117.16 | 117.96 | 100.68% |
| 37 | 62046 | 257.94 | 248.87 | 96.48% |
| 38 | 62030 | 260.08 | 256.97 | 98.80% |
| 39 | 62042 | 202.89 | 197.41 | 97.30% |
| 40 | 61810 | 55.12 | 54.68 | 99.20% |
| | | | Average % | 100.95% |

Figure 3:
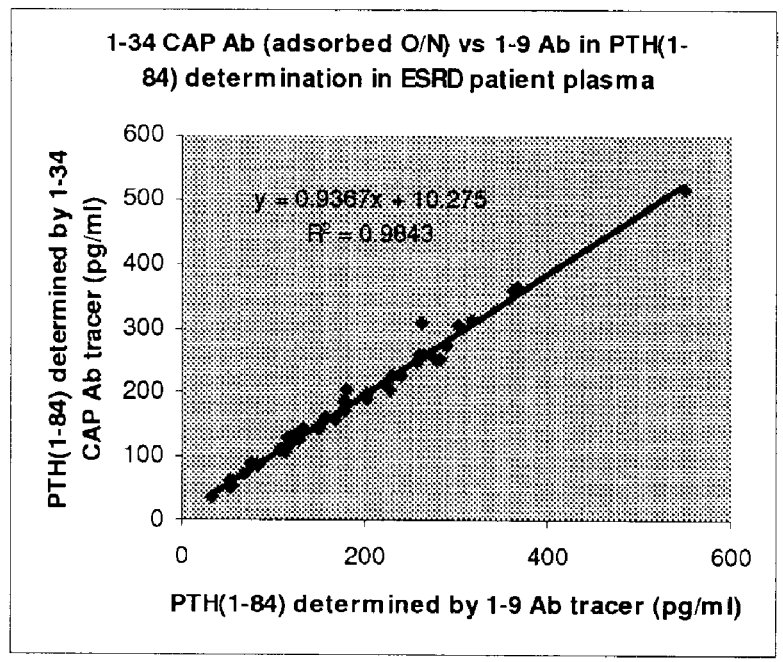
FIG. 3 is a graph showing the correlation between using the $PTH_{1-34}$ CAP antibody (lot G645D) and the anti-$PTH_{1-9}$ antibody (lot G5113C) as tracer antibodies labeled with $^{125}I$ for wPTH determinations in patient plasma. Linear regression statistical analysis of the data leads to an equation $y=0.9367x+10.275$; $R^2=0.9843$, where $y=mx+b$. The $PTH_{1-34}$ CAP antibody was affinity purified on a $PTH_{1-34}$ peptide column using antisera that was generated using $PTH_{1-84}$ as the immunogen and negatively adsorbed overnight at 2-8° C. with an immobilized $PTH_{2-34}$ peptide.

As shown in FIG. 3, the significant correlation ($R^2>0.9$) and the tight slope (0.9-1.1) suggested statistical equivalence in performance of the $PTH_{1-34}$ CAP antibody and the anti-$PTH_{1-9}$ antibody control.

Example 3

Specificity of $PTH_{1-34}$ CAP Antibodies

The $PTH_{1-34}$ CAP antibody was generated as described in Example 1. The $PTH_{1-34}$ CAP antibody was purified with a $PTH_{1-34}$ column and negatively adsorbed with $PTH_{2-34}$ for 3.5 hours to generate G4103B antibody or overnight at 2-8° C. to generate G645D antibody. Cross-reactivity of the $PTH_{1-34}$ CAP antibody to $PTH_{7-84}$ peptide was tested as described in the Directional Insert (SLI 3KI037) for Whole PTH(1-84) Specific IRMA Assay, presented in Example 6. $PTH_{7-84}$ peptide and $PTH_{1-84}$ (SEQ ID NO:1) peptide were purchased from Bachem (Torrance, Calif.) and reconstituted in normal human heat-inactivated serum to make the PTH controls, based on the mass and peptide content provided by Bachem.

Figure 4:
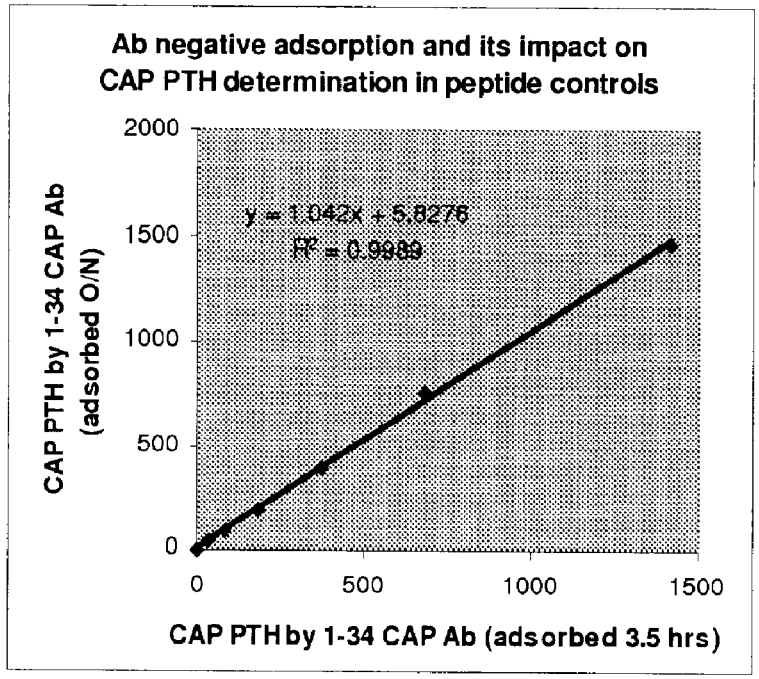
FIG. 4 is a graph showing the correlation between using the $PTH_{1-34}$ CAP antibody G645D (negatively adsorbed with $PTH_{2-34}$ at 2-8° C. overnight) and the $PTH_{1-34}$ CAP antibody G4103B (negatively adsorbed with $PTH_{2-34}$ at room temperature for 3.5 hours) as tracer for wPTH determinations measuring synthetic $PTH_{1-84}$ peptide controls that were prepared by dissolving synthetic $PTH_{1-84}$ peptide in heat-inactivated normal human plasma. Linear regression statistical analysis of the resulting data leads to an equation: y=1.042x+5.8276; $R^2$=0.9989 where y=mx+b.

As shown in Table 4 below, $PTH_{1-34}$ CAP antibody G4103B and G645D reacted with $PTH_{1-84}$ but did not cross-react with PTH$_7$-84. As shown in FIG. 4, the significant correlation (R$^2$>0.9) and the tight slope (0.9-1.1) suggested statistical equivalency of these two antibodies in assay performance. The concentrations of the PTH$_{7-84}$ and PTH$_{1-84}$ (SEQ ID NO:1) controls were measured with the wPTH IRMA assays, using anti-PTH$_{1-34}$ CAP antibody (G403B and/or G645D) as the tracer antibodies. The calculated PTH$_{7-84}$ concentrations for A, B, C, D, E, F, and G were 0 pg/ml, 56.25 pg/ml, 112.5 pg/ml, 225 pg/ml, 450 pg/ml, 900 pg/ml, and 1800 pg/ml, respectively.

TABLE 4

PTH$_{1-34}$ CAP antibody cross-reactivity to PTH$_{7-84}$ peptide

| Controls | CAP PTH (pg/ml) | | |
|---|---|---|---|
| | G4103B | G645D | G4103B/G645D |
| NSB (cpm) | 162 (cpm) | 218 (cpm) | |
| PTH 1-84 A | Below the detectable limit | Below the detectable limit | |
| PTH 1-84 B | 37.09 | 40.77 | 91.0% |
| PTH 1-84 C | 82.25 | 86.43 | 95.2% |
| PTH 1-84 D | 185.97 | 194.78 | 95.5% |
| PTH 1-84 E | 371.21 | 390.12 | 95.2% |
| PTH 1-84 F | 681.43 | 754 | 90.4% |
| PTH 1-84 G | 1414.2 | 1462.8 | 96.7% |
| PTH 7-84 A | 0.49 | 0.47 | |
| PTH 7-84 B | 2.35 | 0.91 | |
| PTH 7-84 C | 0.63 | 1.86 | |
| PTH 7-84 D | 1.61 | 0.92 | |
| PTH 7-84 E | 2.61 | 1.36 | |
| PTH 7-84 F | 2.93 | 2.16 | |
| PTH 7-84 G | 8.13 | 3.5 | |
| AVG | | | 94.0% |

Example 4

Normal Value Range Detected by PTH$_{1-34}$ CAP Antibody

Figure 5:
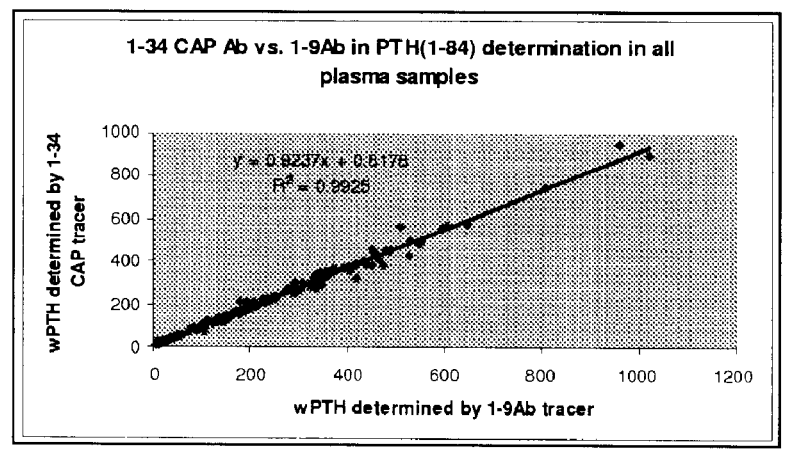
FIG. 5A is a graph showing the correlation between using the $PTH_{1-34}$ CAP antibody (which was negatively absorbed with $PTH_{2-34}$) and the anti-$PTH_{1-9}$ antibody control as iodinated tracer antibodies for wPTH determinations in EDTA plasma samples (including 160 ESRD patient plasma samples and 125 normal plasma samples). Linear regression statistical analysis of the data leads to an equation y=0.9237x+0.8178; $R^2$=0.9925, where y=mx+b. The $PTH_{1-34}$ CAP antibody was affinity purified on a $PTH_{1-34}$ peptide column and negatively adsorbed with an immobilized $PTH_{2-34}$ peptide.
FIG. 5B is a graph showing the correlation between using the $PTH_{1-34}$ CAP antibody and the anti-$PTH_{1-9}$ antibody control as iodinated tracer antibodies for wPTH determinations in 125 normal plasma samples. Linear regression statistical analysis of the data leads to an equation y=0.9648x+0.3291; $R^2$=0.905 where y=mx+b. The $PTH_{1-34}$ CAP antibody was purified on a $PTH_{1-34}$ peptide column and negatively adsorbed with an immobilized $PTH_{2-34}$ peptide.
FIG. 5C is a graph showing the correlation between using the $PTH_{1-34}$ CAP antibody and the anti-$PTH_{1-9}$ antibody as iodinated tracer antibodies for wPTH determination in 160 ESRD patient plasma samples. Statistical analysis of the data leads to an equation y=0.925x+0.3078; $R^2$=0.9877. The $PTH_{1-34}$ CAP antibody was purified on a $PTH_{1-34}$ peptide column and negatively adsorbed with an immobilized $PTH_{2-34}$ peptide.
Figure 5:
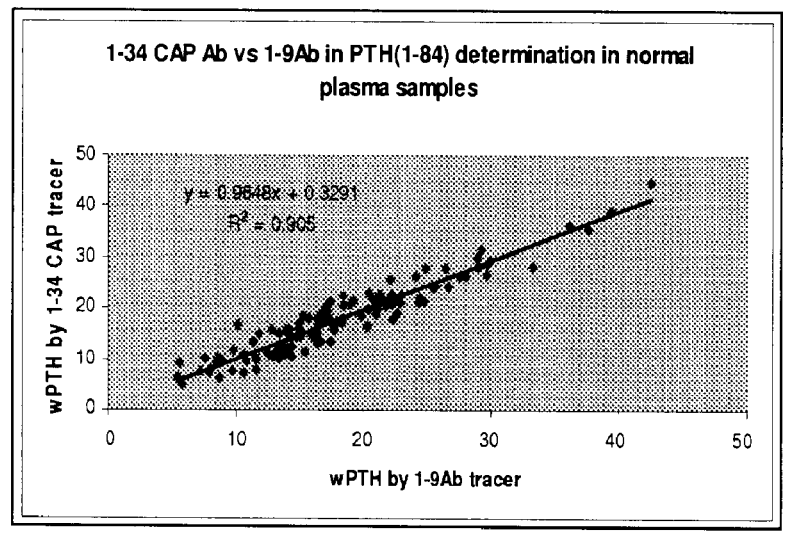
Figure 5:
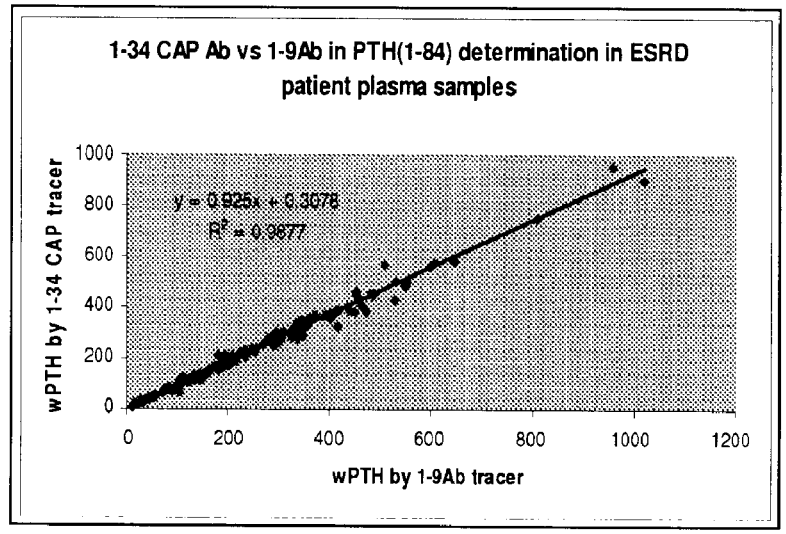

A PTH$_{1-34}$ CAP antibody generated as described in Example 1 was used as tracer for assay comparison with anti-PTH$_{1-9}$ antibody control in PTH IRMA assay. 160 ESRD patient plasma samples and 125 normal samples were tested side-by-side. As shown in FIG. 5, two antibodies demonstrated a close correlation with a slope that was within +/−10%. The 95 percentile of the PTH values in the normal plasma samples was used to determine the Normal Value Range. Both the anti-PTH$_{1-9}$ antibody control and the PTH$_{1-34}$ CAP antibody gave the identical Normal Value Range of 7-36 pg/ml in the whole PTH IRMA assay.

Example 5

Performance Characterization of -PTH$_{1-34}$ CAP Antibody

The detection limit of an assay is defined as the lowest measurable value distinguished from zero, as defined in the Directional Insert (SLI 3KI037) for Whole PTH(1-84) Specific IRMA Assay. In this study three test tracers (E1, E2, and E3) were prepared from 3 lots of PTH$_{1-34}$ CAP antibodies and tested together with an anti-PTH$_{1-9}$ control tracer in a Whole PTH IRMA format as described in the Insert, and in Example 6. As shown in Table 5, the analytical sensitivity for E1, E2 and E3 in the assays is comparable to that of the control tracer prepared from PTH$_{1-9}$ antibody.

TABLE 5

Analytical sensitivity

| Tracers | Antibody used | Sensitivity (pg/ml) | Average (pg/ml) |
|---|---|---|---|
| Control | 1-9 Ab | 1.87 | 1.87 |
| E1 | (1-34) CAP Ab | 1.87 | |
| E2 | (1-34) CAP Ab | 0.85 | 1.6 |
| E3 | (1-34) CAP Ab | 2.1 | |

Sample dilution linearity for PTH$_{1-34}$ CAP was also tested. Three ESRD patient plasma samples were used for dilution linearity. The samples were diluted in Calibrator 0 and their whole PTH concentrations were determined using a PTH$_{1-34}$ CAP antibody as tracer in the whole PTH IRMA assay. As shown in Table 6, the average recovery was within +/−7%, indicating an excellent linearity in recovery.

TABLE 6

Sample dilution linearity for PTH$_{1-34}$ CAP antibody as tracer

| Patient Plasma | Dilution | Expected (pg/ml) | Found (pg/ml) | Recovery (%) | AVG recovery |
|---|---|---|---|---|---|
| A | 1 | 335.61 | 335.61 | | |
| | 2 | 167.81 | 159.76 | 95.2% | |
| | 4 | 83.90 | 81.1 | 96.7% | |
| | 8 | 41.95 | 37.53 | 89.5% | |
| | AVG | | | | 93.8% |
| B | 1 | 448.1 | 448.1 | | |
| | 2 | 224.05 | 254.73 | 113.7% | |
| | 4 | 112.025 | 106.07 | 94.7% | |
| | 8 | 56.0125 | 45.74 | 81.7% | |
| | AVG | | | | 96.7% |
| C | 1 | 956.96 | 956.96 | | |
| | 2 | 478.48 | 488.93 | 102.2% | |
| | 4 | 239.24 | 210.56 | 88.0% | |
| | 8 | 119.62 | 113.96 | 95.3% | |
| | AVG | | | | 95.2% |

Figure 6:
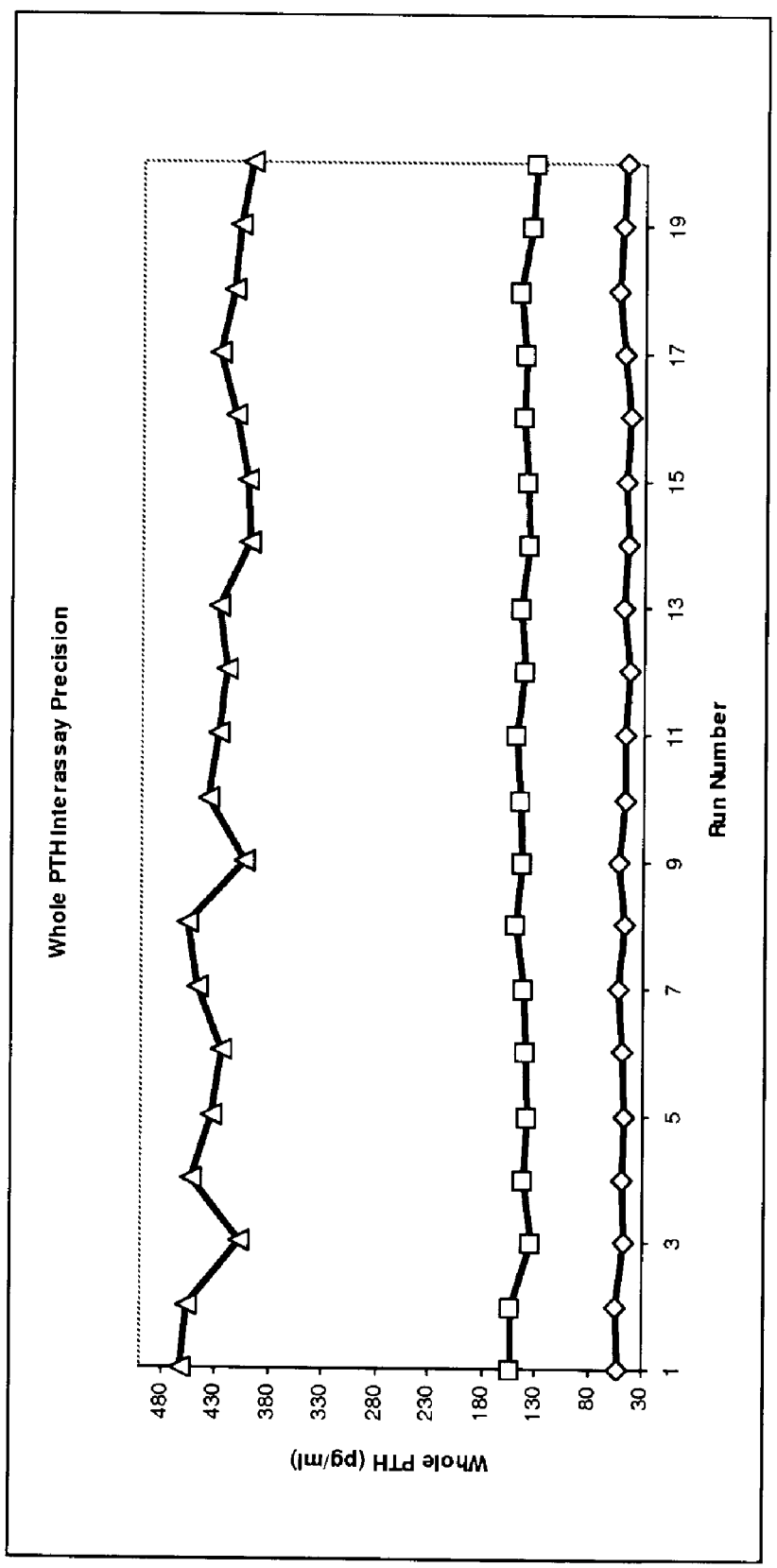
FIG. 6 is a graph showing the whole PTH inter-assay precision for three pooled ESRD patient plasma samples in 20 separate runs over a period of three weeks using the $PTH_{1-34}$ CAP antibody (which was affinity purified with a $PTH_{1-34}$ peptide column and negatively absorbed at room temperature for 3.5 hours with an immobilized $PTH_{2-34}$ peptide) as iodinated tracer antibody in the whole PTH IRMA. Δ shows testing results from a pooled ESRD patient plasma sample with high PTH level; □ shows testing results from a pooled ESRD patient plasma sample with medium PTH level; and shows testing results from a pooled ESRD patient plasma sample with low PTH level.
Figure 7:
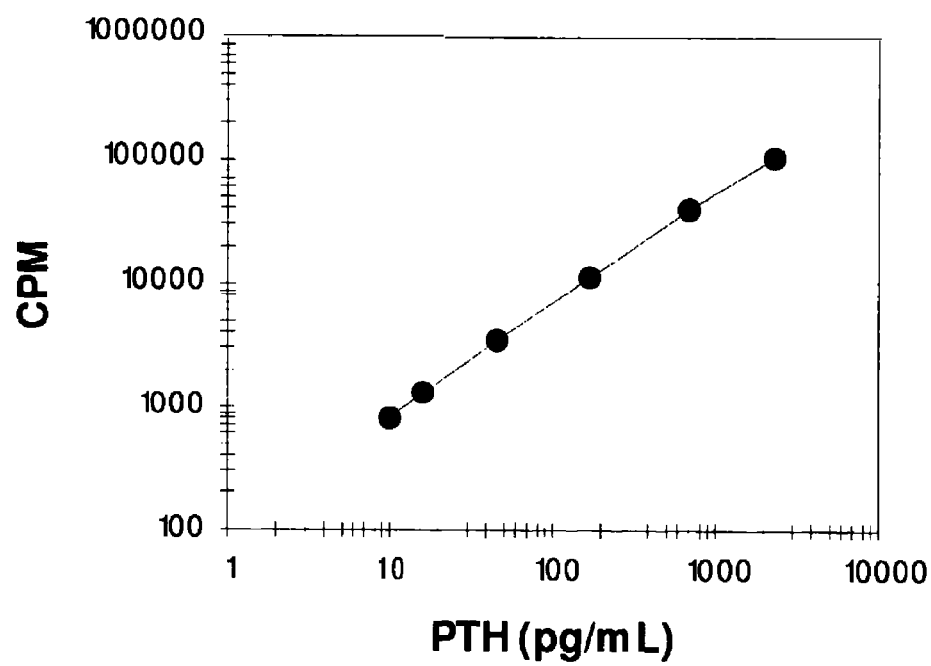
FIG. 7 is a graph showing a representative standard curve.

Whole PTH inter-assay precision using PTH$_{1-34}$ CAP antibody as tracer was also tested. Three ESRD patient plasma samples were tested in 20 separate runs over a period of three weeks, using the PTH$_{1-34}$ CAP antibody as tracer. The results are shown in FIG. 6. The average CV (coefficient of variation) for each sample was below 7%, indicating an acceptable inter-assay precision (an acceptable inter-assay precision is CV less than 10%).

Example 6

Whole PTH (1-84) Specific Scantibodies
Immunoradiometric (IRMA) Assay
(Coated Bead-Technology) (Part Number: 3KG056)
For the quantitative determination of human whole PTH
For In Vitro Diagnostic Use Only Store at 2-8° C.
 Intended Use
 This kit has been designed for the quantitative determination of human whole parathyroid hormone (PTH) without cross-reaction to PTH (7-84) fragment in blood samples.[32,33,34,35]
 Physiology
 The Whole PTH peptide (1-84) (SEQ ID NO:1) is secreted by parathyroid glands under the regulation of the extra-cellular concentration of ionized calcium, vitamin D and magnesium. PTH acts with respect to calcium on the kidney and the skeleton[4,5]. PTH binds to receptors, which stimulate adenylate-cyclase to produce cyclic adenosine monophosphate (cAMP) from adenosine triphosphate (ATP)[10,13]. The biological activity of PTH resides in the first 3 amino acids of the N-terminal portion of the molecule. PTH is metabolized either intra glandular or in the peripheral organs into fragments. Circulatory PTH is immunologically heterogeneous[7,6,12,13,18,19]. A recent study of circulation immunoreactive PTH showed that significant amounts of a large carboxyl-terminal PTH fragment, PTH (7-84), presented in blood samples from uremic patients[31].

Biologically inactive fragments with molecular weights of 4000-7000 Daltons circulate with a half-life of 30 minutes in healthy persons[4,5].

cAMP or other PTH dependent processed metabolites (e.g. hypophosphatemia) stimulate the renal hydroxylation of 25-(OH) vitamin D to 1,25-$(OH)_2$ vitamin D. This vitamin D metabolite stimulates calcium absorption by the small intestine. Severe vitamin D deficiency results in an enhanced secretion of PTH compared to the secretion of calcium. Hypomagnesaemia in the primary stage stimulates hypocalcemia. Severe hypomagnesaemia results in the reduced secretion of PTH.

Primary and secondary hyperparathyroidism, kidney insufficiency, malabsorption-syndrome and pseudo-hypoparathyroidism result in elevated concentrations of PTH[14,15,16]. Decreased concentrations of PTH coincide with high doses of vitamin-D, milk-alkali-syndrome, Morbus Boeck, hyperthyreosis, ingestion of thiazide and hypercalcemia of malignancy. PTH concentration is also decreased with absorptive hypercalciuria and hypoparathyroidism.

Principle of Procedure

Scantibodies Whole PTH Kit is an immunoradiometric (IRMA) assay utilizing polyclonal PTH antibodies directed against N-terminal PTH and C-terminal PTH. The use of these antibodies guarantees that only Whole PTH (CAP) is detected. The anti-PTH N-terminal region specific antibody is labeled with $^{125}$I. The antibody directed against C-terminal PTH (39-84 fragment) is fixed to the beads. Whole PTH (CAP) in patient samples is bound both to the beads and to the $^{125}$I-anti N-terminal PTH. After incubation, free $^{125}$I-antibodies and bound $^{125}$I-antibodies fractions are separated by discarding the supernatant. Simple wash steps reduce the non-specific binding (NSB) to a minimum for increased precision at the low end of the calibration curve. The concentration of Whole PTH (CAP) is directly proportional to the radioactivity bound to the beads after separation. The concentration of PTH in unknown patient samples and controls is determined by interpolation using a calibration curve.[30]

Reagents

The Scantibodies Whole PTH Kit contains sufficient reagents for 100 single determinations. The kit is stable at 2°-8° C. until the stated expiration date.

PTH Calibrators

One set of calibrators consists of seven vials containing lyophilized human serum with nominal Whole PTH (CAP) concentrations. The lyophilized calibrators are prepared in stabilized human serum containing sodium azide 0.1% (w/v). The Whole PTH (CAP) concentrations are declared on the vial label.

PTH Controls

One set of controls consists of two vials containing Whole PTH (CAP) in lyophilized human serum with 0.1% (w/v) sodium azide. The concentration ranges of Whole PTH (CAP) are declared on the vial labels.

$^{125}$I-Anti N-Terminal PTH Tracer

One set of tracer consists of two bottles of $^{125}$I-antibodies. Each bottle contains goat anti N-terminal PTH antibodies which are labeled with $^{125}$I and dissolved in 5 ml phosphate buffered saline with sodium azide 0.1% (w/v) and protein stabilizers. The maximum radioactivity in a bottle is <370 kBq (<10 μCi).

PTH (39-84) Antibody Coated Beads

One bottle contains 100 polystyrene beads (8 mm) plus desiccant. The beads are coated with goat anti-PTH (39-84). The desiccant contains silica.

Wash Concentrate

One bottle contains 30 ml of a 30 fold concentrate of phosphate buffered saline with sodium azide 1.5% (w/v) and detergent.

Preparation and Storage of Reagents

PTH Calibrators

The Scantibodies Laboratory, Inc. Whole PTH Coated Bead Diagnostic Kit contains the PTH standards prepared analytically on a mass basis from purified synthetic Whole PTH (1-84) (SEQ ID NO:1). These standards are further evaluated against "primary standards" which are stored at −70° C. to maintain calibration.

Reconstitute the zero calibrator with 5 ml of distilled or deionized water. Reconstitute the remaining calibrators with 2 ml of distilled or deionized water. After addition of the water, mix each vial thoroughly but gently. Use the reconstituted calibrators within 1 hour. Store the unused portion of the calibrators below −20° C. until the stated expiration date. Do not store the calibrators at room temperature for more than one hour at any given time. Do not thaw any calibrator vial more than two times.

PTH Controls

Reconstitute the vials of controls with 2 ml of distilled or deionized water. After addition of the water, mix each vial thoroughly but gently. Use the reconstituted controls within 1 hour. Store the unused portion of the controls below −20° C. until the stated expiration date. Do not store the controls at room temperature for more than one hour at any given time. Do not thaw any control vial more than two times.

$^{125}$I-Anti N-Terminal PTH Tracer

The tracer is ready to use. Store the tracer at 2°-8° C. until the stated expiration date.

PTH (39-84) Antibody Coated Beads

The antibody coated beads are ready to use. Store the beads at 2°-8° C. until the stated expiration date. Allow the beads to equilibrate to ambient temperature prior to opening package. Reseal the package immediately after removing the required number of beads.

Wash Concentrate

Mix the contents of the wash concentrate thoroughly with 870 ml of distilled or deionized water (1:30). Store the diluted wash solution at room temperature (18°-25° C.) until the stated expiration date.

Warnings and Precautions for Users

Use of the Assay

The reagents are for in vitro diagnostic use only.

Human Serum Caution

The human serum in this kit has been prepared from human donors and it has been tested by FDA approved immunoassays and found to be non-reactive for Hepatitis B Surface Antigen (HBsAg), Anti HIV I/II and Anti HCV. However, it is recommended to consider the calibrators and controls as a potential biohazard and handle them with the same precautions as applied to any untested patient sample.

Radioactivity Warning

This radioactive material may be received, acquired, possessed, or used only by physicians, clinical laboratories, or hospitals and only for in vitro clinical or laboratory tests not involving internal or external administration of the material, or the radiation therefrom, to human beings or animals. Its receipt, acquisition, possession, use and transfer are subject to the regulations and a general license of the U.S. Nuclear Regulatory Commission or of a state with which the Commission has entered into an agreement for the exercise of regulatory authority.

All radioactive materials must be disposed of according to the regulations (regulations differ from country to country) and guidelines of the agencies with jurisdiction over the laboratory. Do not eat, drink, smoke or apply cosmetics in areas where radioactive materials are used. Storage of radioactive materials should be limited to specifically designated and appropriately secured areas. Access to radioactive materials should be limited to authorized and trained personnel only. Do not pipette radioactive solutions by mouth. Avoid direct contact with radioactive materials by using protective articles such as lab coats and disposable gloves. Radioactive materials must be stored in designated areas in their original containers or in containers providing equivalent radiation protection. A record of disposal of all radioactive materials must be kept. Immediately remove spilled solutions and decontaminate contaminated devices. Check laboratory equipment and glassware regularly to detect contamination with radioisotopes.

Sodium Azide (NaN$_3$) Warning

Some reagents in the Scantibodies PTH assay contain sodium azide. Sodium azide may react with lead and copper plumbing to form highly explosive metal azides. On disposal flush the drain with a large volume of water to prevent azide build-up. Avoid direct contact with skin and mucous membranes.

Sample Preparation and Storage

Specimen Collection

The determination of human PTH should be made on EDTA-plasma. Four hundred microliters of plasma are required to assay one sample in duplicate. To obtain plasma, collect blood by venipuncture into a tube containing EDTA. Centrifuge the sample and separate the plasma from the cells. Plasma should be stored at −20° C. or lower. Avoid repeated freezing and thawing of plasma. Do not use patient samples which have been frozen and thawed more than two times.

Dilution of Patient Samples

Dilute plasma samples with PTH concentrations greater than the highest calibrator with Scantibodies PTH Zero Calibrator before assay. The dilution factor is applied to the diluted sample assay result in order to determine the PTH concentration in the undiluted sample.

Quality Control

Two levels of controls are provided with each assay kit. The values assigned to these controls are printed on the container label. The control value should fall within the specified range when tested in the same manner as the unknowns. Controls should be included in each assay. If the control values do not meet the established range, the assay may be invalid and should be repeated.

Assay Procedure

Materials Provided

The Scantibodies Whole PTH Kit (Part No. 3KG056) is supplied with the following:

| Description | Number |
| --- | --- |
| PTH Standards 3CA650, 3CB650, 3CC650, 3CD650, 3CE650, 3CF650, 3CG650 | 7 vials |
| PTH Controls Part Nos. 3CA651, 3CB651 | 2 vials |
| PTH (39-84) Antibody Coated Beads Part No. 3KB001 | 1 bottle of 100 beads |
| Goat Anti-N-Terminal PTH $^{125}$I Antibody Part No. 3KL022 | 2 vials |
| Wash Concentrate Part No. 3KW001 | 1 bottle |
| Directional Insert Part No. 3KI037 | 1 insert |

Materials And Equipment Required But Not Provided:
Distilled or deionized water
Round-bottomed polypropylene or polystyrene test tubes (12×55, 12×75, 12×70 mm or equivalent)
Pipettor with disposable tips: 0.2 ml
Wash station
Vortex mixer
VWR orbital shaker Model DS-500 or equivalent
Gamma counter calibrated to detect $^{125}$I
Preparation for Assay For each assay, prepare the following groups of tubes and place them in a test tube rack (double determination):
  2 total count tubes (optional for QC). Use non-coated tubes.
  2 Bo tubes (NSB)
  2 tubes for each calibrator concentration
  2 tubes for each control concentration
  2 tubes for each patient sample Pipetting and Incubation Steps Pipette 0.2 ml of calibrators, samples and controls into the corresponding tubes.

Pipette 0.1 ml of goat anti-N-terminal PTH $^{125}$I antibody into each tube.

Gently vortex all tubes.

Dispense one antibody coated bead into each tube except for the total count tubes. To add the beads, tilt the test tube rack to approximately a 30 degree angle to prevent splashing.

Seal the tubes and incubate them for 180°-24 hours at room temperature (180-25° C.) and shaking 170 RPM.

Aspirate the supernatant from each tube except for the total count tubes. Wash the beads 3 times with 2 ml of diluted wash solution. After each addition of diluted wash solution aspirate all of the wash solution.

Count each tube for at least 1 minute in a gamma counter calibrated to detect $^{125}$I. The total count tube should contain approximately 300,000 CPM (assuming the counter has an efficiency of 70%-80%) when freshly iodinated $^{125}$I-anti-N-terminal PTH tracer is used. The total activity of the tracer decreases according to the half-life of $^{125}$I.

| PIPETTING GUIDE | | | | | |
| --- | --- | --- | --- | --- | --- |
| Additive to Tube | Total Count Tubes | Bo Tubes | Calibrator Tubes | Control Tubes | Sample Tubes |
| Calibrator | — | 200 µl | 200 µl | — | — |
| Control | — | — | — | 200 µl | — |
| Sample | — | — | — | — | 200 µl |
| $^{125}$I anti-N-terminal PTH | 100 µl | 100 µl | 100 µl | 100 µl | 100 µl |
| Beads | — | 1 | 1 | 1 | 1 |

Vortex mix all tubes, except for the TC tubes. Incubate tubes for 18-24 hours at room temperature (18°-25° C.) and shaking at 170 RPM.
Aspirate the supernatant from all of the tubes except the total count tubes. Wash all tubes except the total count tubes by adding 2 ml of diluted wash solution and aspirating the wash solution. Repeat this wash step two more times for a total of three times.
Count each tube for at least 1 minute in a gamma counter.

Procedural Comments

Interferences:

Samples containing up to 250 mg/dl triglyceride, 15 mg/dl hemoglobin and 7.5 mg/dl bilirubin do not exhibit any effect on the assay.

Grossly hemolyzed or lipemic samples.

Samples from patients receiving radioisotopes for diagnostic or therapeutic purposes.

Contamination of the sample or assay tube with $^{125}$I or other radioisotopes.

Reagents from different lot numbers must not be interchanged.

The patient sample or calibrator and the $^{125}$I-anti-N-terminal PTH tracer should be pipetted carefully into the bottom one-fourth of the assay tube. This is to avoid losing liquid on the surface of the tube as the liquid runs down the tube.

The washing step is an important step in the assay procedure. Accurate dispensing of the wash solution and complete aspiration of the tube contents is essential to achieving assay sensitivity, low background and assay precision.

It is recommended that calibrators and patient samples be assayed in duplicate. The average counts per minute of each duplicate should then be used for data reduction and the calculation of results.

Avoid sample to sample contamination by using a new pipette tip for each sample.

Calculation of Results

Evaluation

Calculate the average CPM for each double determination.

Subtract the average CPM of the zero calibrator tubes from the CPM's from all other tubes in order to obtain the corrected CPM for each tube.

Corrected CPM=average CPM of duplicate samples—average CPM of duplicate zero calibrators.

Draw the calibration curve by plotting the average corrected CPM from each duplicate calibrator level (ordinate) against the respective concentration declared on the calibrator vial (absolute) using log-log graph paper. Obtain sample concentrations by interpolation of average sample CPM on the calibration curve.

If samples were run with dilution, multiply the diluted sample assay results from the curve by the appropriate dilution factors to obtain the undiluted sample assay results.

| Sample Data | | | |
|---|---|---|---|
| Tube | CPM | Ave. CPM | Corrected CPM |
| Total Activity | 331856 | 332415 | |
| | 332975 | | |
| 0 pg/ml | 246 | 264 | |
| | 283 | | |
| 10 pg/ml | 787 | 819 | 555 |
| | 852 | | |
| 16 pg/ml | 1349 | 1306 | 1042 |
| | 1262 | | |
| 46 pg/ml | 3490 | 3523 | 3259 |
| | 3557 | | |
| 165 pg/ml | 11178 | 11124 | 10860 |
| | 11070 | | |
| 700 pg/ml | 39835 | 39871 | 39607 |
| | 39907 | | |
| 2300 pg/ml | 110979 | 110574 | 110310 |
| | 110168 | | |

NOTE:
The data presented are for demonstration purposes only and must not be used in place of data generated at the time of the assay.

Automated data reduction can also be used to construct the Scantibodies PTH calibration curve. To program automated data reduction systems or to adapt an existing program consult the data processor manufacturer or the programmer.

Limitations of the Procedure

For diagnostic purposes PTH values should be used in addition to other diagnostic data and clinical information available to the physician.

The assay procedure must be followed exactly; careful technique must be used to obtain valid results. Any modification of the assay procedure is likely to alter the results.

Grossly hemolyzed, lipemic or icteric samples are likely to give non valid results.

The highest concentration of PTH measurable without sample dilution is the concentration of the highest calibrator. The lowest level measurable is approximately 1 pg/ml.

Expected Values

The normal value range was determined following the NCCLS guidelines (C28-A). using 128 samples from apparently healthy individuals. It is recommended that each laboratory establish its own range of normal values. The values given are only indicative and may vary from other published data.

| PATIENT CLASSIFICATION | Whole PTH RANGE pg/ml |
|---|---|
| Normal | 5-39 |
| Hyperparathyroidism | >39 |

Performance Characteristics

Accuracy, Recovery

Different samples with low concentrations of PTH were spiked with 2 amounts of PTH. The % recovery was determined following assay of the spiked samples.

| Sample value (pg/ml) | Added PTH (pg/ml) | Measured value (pg/ml) | Expected value (pg/ml) | Recovery (%) |
|---|---|---|---|---|
| 36.05 | — | — | — | — |
| | 50.07 | 43.11 | 43.06 | 100.12 |
| | 141.51 | 90.62 | 88.78 | 102.07 |
| 77.09 | — | — | — | — |
| | 41.34 | 66.9 | 59.22 | 112.98 |
| | 130.31 | 108.72 | 103.7 | 104.84 |
| 126.2 | — | — | — | — |
| | 39.23 | 91.42 | 82.72 | 110.52 |
| | 130.33 | 127.38 | 128.27 | 99.31 |

Accuracy Dilution

Different samples with high concentrations of PTH were diluted in a sample with low concentrations of PTH. The % recovery was determined following assay of the diluted samples.

| Sample | Dilution | Measured value (pg/ml) | Expected value (pg/ml) | Recovery % |
|---|---|---|---|---|
| 1 | Neat | 2057. | | |
| | 1:2 | 51053.58 | 1028.75 | 102 |
| | 1:4 | 519.13 | 514.38 | 101 |
| | 1:8 | 273.32 | 257.19 | 106 |

-continued

| Sample | Dilution | Measured value (pg/ml) | Expected value (pg/ml) | Recovery % |
|---|---|---|---|---|
| 2 | Neat | 1595.35 | | |
|   | 1:2 | 758.28 | 797.68 | 95 |
|   | 1:4 | 395.67 | 398.84 | 99 |
|   | 1:8 | 210.98 | 199.42 | 106 |
| 3 | Neat | 1006.36 | | |
|   | 1:2 | 485.9 | 503.18 | 97 |
|   | 1:4 | 256.29 | 251.59 | 102 |
|   | 1:8 | 140.6 | 125.80 | 112 |
| 4 | Neat | 646.09 | | |
|   | 1:2 | 333.07 | 323.05 | 103 |
|   | 1:4 | 168.56 | 161.52 | 104 |
|   | 1:8 | 87.11 | 80.76 | 108 |
| 5 | Neat | 573.91 | | |
|   | 1:2 | 303.99 | 286.96 | 106 |
|   | 1:4 | 159.69 | 143.48 | 111 |
|   | 1:8 | 86.04 | 71.74 | 120 |
| 6 | Neat | 181 | | |
|   | 1:2 | 97.82 | 90.50 | 108 |
|   | 1:4 | 48.02 | 45.25 | 106 |
|   | 1:8 | 20.42 | 22.63 | 90 |
| 7 | Neat | 153.12 | | |
|   | 1:2 | 91.05 | 76.56 | 119 |
|   | 1:4 | 49.59 | 38.28 | 130 |
|   | 1:8 | 22.28 | 19.14 | 116 |

High Dose Hook Response

This high dose hook response of the Scantibodies Laboratory, Inc. Whole PTH Specific Coated Bead Diagnostic Kit was determined as 20,000 pg/ml of Whole PTH (CAP). Samples greater than the highest standard (approximately 2300 pg/ml) and up to 20,000 pg/ml Whole PTH (CAP) will read CPM values greater than that of the highest standard.

Precision

The inter-assay precision was evaluated by performing 20 separate Whole PTH (CAP) assays on two samples in duplicate over a two week period.

Precision Inter-assay

| Kit Batch | Sample | Mean value (pg/ml) | SD (pg/ml) | % CV |
|---|---|---|---|---|
| E2 | 1 | 32.75 | 2.54 | 7.76 |
| E2 | 2 | 285.05 | 11.81 | 4.14 |
| E3 | 1 | 30.97 | 2.15 | 6.95 |
| E3 | 2 | 310.26 | 9.08 | 2.93 |

The intra-assay precision was evaluated by performing 20 replicates in the Whole PTH (CAP) assays on two samples.

Precision Intra-assay

| Kit Batch | Sample | Mean value (pg/ml) | SD (pg/ml) | % CV |
|---|---|---|---|---|
| E1 | 1 | 30.3 | 1.5 | 4.94 |
| E1 | 2 | 283.87 | 7.49 | 2.64 |
| E2 | 1 | 30.85 | 1.27 | 4.13 |
| E2 | 2 | 273.33 | 6.3 | 2.3 |
| E3 | 1 | 29.33 | 1.77 | 6.05 |
| E3 | 2 | 290.78 | 7.43 | 2.56 |

Sensitivity

The detection limit of the assay is defined as the lowest measurable value distinguishable from zero. This sensitivity was determined by assaying the zero calibrator 20 times in the same assay. The detection limit is approximately 1.0 pg/ml at 2 standard deviation above the PTH zero calibrator.

Specificity

This Whole PTH (CAP) assay does not show any cross-reaction to PTH (7-84) fragment when the synthetic PTH (7-84) peptide is serially diluted with standard zero matrix and assayed.

| PTH (7-84) Conc. Sample (pg/ml) | Measured PTH conc. (pg/ml) |
|---|---|
| 2500 | undetectable |
| 5000 | undetectable |
| 10000 | undetectable |
| 20000 | undetectable |

A high degree of correlation exists between the PTH levels of duplicate samples measured by a commercially available predicate PTH kit and those levels measured by the Scantibodies Laboratory, Inc. (SLI) Whole PTH (1-84) (CAP) Specific IRMA Assay. A correlation coefficient (r) of 0.98 (n=223) was obtained with a slope of 1.47 and intercept of −13.65 where x represents the predicate device data and y represents the SLI data. Calculations were made with samples ranging from 9.6-1808 pg/mL.

REFERENCES

1. Berson, S. A., Yalow, R. S., Aurbach, G. D., and Potts Jr., J. T. "Immunoassay of Bovine and Human Parathyroid Hormone." Proc. National Academy Science, U.S.A. 49:613-617, 1963.
2. Keutmann, H. T., Sauer, M. M., Hendy, G. N., O'Riordan, J. L. H., and Potts Jr., J. T. "Complete Amino Acid Sequence of Human Parathyroid Hormone." Biochemistry 17:5723-5729, 1978.
3. Raisz, L. G., Yajnik, C. H. Bockman, R. S., and Bower, B. B. "Comparison of Commercially Available Parathyroid Hormone Immunoassay in the Differential Diagnosis of Hypercalcemia Due to Primary Hyperparathyroidism or Malignancy." Annals International Medicine 91:739-740, 1979.
4. Habener, J. F., and Potts Jr., J. T. "Biosynthesis of Parathyroid Hormone." New England Journal of Medicine 299: 580-585, and 635-644, 1978.
5. Segre, G. V., D'Amour, P. D., Hultman, A., and Potts Jr., J. T. "Effects of Hepatectomy and Nephrectomy Uremia on Metabolism of Parathyroid Hormone in the Rat." Journal of Clinical Investigation 67:439-448, 1981.
6. Segre, G. V., Perkins, A. S., Witters, L. A., and Potts Jr., J. T. "Metabolism of Parathyroid Hormone by Isolated Kupffer Cells and Hepatocytes." Journal Clinical Investigations 67:449-457, 1981.
7. Segre, G. V., Habener, J. F., Powell, D., Tregear, G. W., and Potts Jr., J. T. "Parathyroid Hormone in Human Plasma: Immunochemical Characterization and Biological Implications." Journal of Clinical Investigations 51:3163-3172, 1972.
8. Freitag, J., Martin, K. J., Hruska, K. A., Anderson, C., Conrades, M., Ladenson, J., Klahr, S. and Slatopolsky, E. "Impaired Parathyroid Hormone Metabolism in Patients with Chronic Renal Failure." New England Medical Journal of Medicine 298:29-32, 1978.
9. Potts Jr., J. T., Segre, G. V. and Endres, D. B. "Current Clinical Concepts: Assessment of Parathyroid Function with an N-Terminal Specific Radioimmunoassay for Intact Parathyroid Hormone." Nichols Institute Reference Laboratories, 1983.
10. Goltzman, D., Henderson, B., and Loveridge, N. "Cytochemical Bioassay of Parathyroid Hormone: Characteristics of the Assay and Analysis of Circulating Hormonal Forms." Journal of Clinical Investigations 65:1309, 1980.
11. Lafferty, F. W. "Pseudohyperparathyroidism." Medicine 45:247, 1966.
12. Endres, D., Brickmnan, A., Goodman, W., Maloney, D., and Sherrard, D. "N-Terminal PTH Radioimmunoassays in Assessment of Renal Osteodystrophy." Kidney International 21:132, 1982.
13. Broadus, A. E., Mahaffey, J. E., Bartter, F. C., and Neer, P. M. "Nephrogenous Cyclic Adenosine Monophosphate as a Parathyroid Function Test." Journal of Clinical Investigations 60:771, 1977.
14. Berson, S. A., Yalow, R. S., Bauman, A., Rothchild, M. A. and Newerly, K. Journal of Clinical Investigations 35:170, 1956.
15. Rodbard, D., Rayford, P. L., Cooper, J. A. and Ross, G. T. Journal of Clinical Endocrinology Metab. 28:1412, 1968.
16. Segre, G. V. Niall, H. D., Habener, J. F., and Potts Jr., J. T. American Journal of Medicine 56:774.
17. Flueck, J., Edis, A., McMahon, J. and Arnaud, C. "Proceedings of the 58th American Meeting of the Endocrine Society." June 1976.
18. Silverman, R. and Yalow, R. S. Journal of Clinical Investigations 52:1958, 1973.
19. Segre, G. V., Niall, H. D., Sauer, R. T. and Potts Jr., J. T. Biochemistry 16:2417, 1977.
20. Canterbury, J. M., Bricker, L. A., Levy, G. S., Kozlovskis, et. al. Journal of Clinical Investigations 55:1245, 1975.
21. Mallette, L. E., Tuma, S. N., Berger, R. E. and Kirkland, J. L. "Radioimmunoassay for the Middle Region of Human Parathyroid Hormone Using a Homologous Antiserum with a Carboxyl-terminal Fragment of Bovine Parathyroid Hormone as Radioligand." Journal of Clinical Endocrinology Metab. 54:1017, 1982.
22. Roos, B. A., Lindall, A. W., Aron, J. W., et al. "Detection and Characterization of Small Mid-Region Parathyroid Hormone Fragments in Normal and Hyperparathyroid Glands and Sera by Immuno-Extraction and Region Specific Radioimmunoassays." Journal of Clinical Endocrinology Metab. 53:709, 1981.
23. Gallagher, J. C., Riggs, B. L., Jerpbak, C. M. and Arnaud, C. D. "The Effect of Age on Serum Immunoreactive Parathyroid Hormone in Normal and Osteoporotic Women." Journal Of Laboratory Clinical Medicine 95:373, 1980.
24. Mallette, L. E. "Use of Homologous Antisera for Radioimmunoassay of Human Parathyroid Hormone." Ligand Review 1:18, 1979.
25. Dambacher, M. A., Fischer, J. A., Hunziker, W. H. et. al. "Distribution of Circulating Immunoreactive Components of Parathyroid Hormone in Normal Subjects and in Patients with Primary and Secondary Hyperparathyroidism: The Role of the Kidney and of the Serum Calcium Concentration." Clinical Science 57:435, 1979.
26. Wood, W. G., Butz, R., Casaretto, M., et. al. "Preliminary Results on the Use of an Anti-serum to Human Parathyrin in a Homologous Radioimmunoassay." Journal of Clinical Chemical Biochemistry 18:789, 1980.
27. Kao, P. C., Jiang, N. S., Klee, G. G., and Purnell, D. C. "Development and Validation of a New Radioimmunoassay for Parathyrin (PTH)." Clinical Chemistry 28:69, 1982.
28. Travis, J. C. (ed.) "Clinical Radioimmunoassay." State-of-the-Art Scientific Newsletter, Inc., Anaheim, Calif. 92803, 1980.
29. Rodbard, D., and Hutt, D. "Statistical Analysis of Radioimmunoassays and Immunoradiometric (labeled antibody) Assays." Assays, Radioimmunoassays and Related Procedures in Medicine, Vol. 1 Vienna: International Atomic Energy Agency, Vienna, 1974.
30. Nussbaum, S. R., Zahradnik, R. J., Lavigne, J. R., Brennan, G. L., Nozawa-Ung, K., Kim, L. Y., Kentmann, H. T., Wang, C. A., Potts Jr., J. T. and Segre, G. V. "Highly Sensitive Two-Site Immunoradiometric Assay of Parathyrin and Its Clinical Utility in Evaluating Patients with Hypercalcemia." Clinical Chemistry Vol. 33, No. 8, 1364-1367, 1988.
31. Lepage R., Roy L., Brossard J. H., Rousseau L., Dorais C., Lazure C., D=Amour P. AA Non-(1-84) Circulating Parathyroid Hormone (PTH) Fragment Interferes Significantly with Intact PTH Commercial Assay Measurements in Uremic Samples.≅Clinical Chemistry Vol. 44, No. 4, 805-809, 1998.
32. Gao, P., Scheibel, S., D=Amour, P., Cantor, T. L. A Measuring the Biologically Active or Authentic Whole Parathyroid Hormone (PTH) with a Novel Immunoradiometric Assay Without Cross-reaction to the PTH(7-84) Fragment.≅Journal of Bone and Mineral Research 14:S446, 1999.
33. Brossard, J. H., Lepage, R., Gao, P., Cantor, T., Rousseau, L., D=Amour, P. AA New Commercial Whole-PTH Assay Free of Interference by Non-(1-84) Parathyroid Hormone (PTH) Fragments in Uremic Samples.≅Journal of Bone and Mineral Research 14:S444, 1999.
34. Slatopolsky, E., Finch, J. L., Martin, D., Sicard, G., Gao, P., Cantor, T. "A Novel Mechanism for Skeletal Resistance in Uremia." Journal of American Society of Nephrology 10:625A, 1999.
35. John, M. R., Goodman, W. G., Gao, P., Cantor, T. L., Salusky, I. B., Jueppner, H. AA Novel Immunoradiometric Assay Detects Full-length Human PTH but Not Amino-terminally Truncated Fragments: Implication for PTH Measurements in Renal Failure.≅The Journal of Clinical Endocrinology & Metabolism 84:4287, 1999.
36. Brossard J. H., Lepage R., Roy L., Rousseau L., Dorais C., Lazure C., D=Amour P. AInfluence of Glomerular Filtration Rate on Non-(1-84) Parathyroid Hormone (PTH) Detected by Intact PTH Assays.≅Clinical Chemistry Vol. 46:5, 697-703, 2000.

Although the foregoing invention has been described in some detail by way of illustration and example for purposes of clarity of understanding, the descriptions and examples should not be construed as limiting the scope of the invention.

The invention claimed is:

1. A method of generating an antibody that specifically binds to a target parathyroid hormone (PTH) peptide, said method comprising:
   a) introducing a PTH peptide immunogen to a mammal in an amount sufficient to produce an antibody to said PTH peptide immunogen; wherein said PTH peptide immunogen has an amino acid sequence which starts at amino acid position 1 and ends at amino acid position 84 of a whole PTH;
   wherein the whole PTH has the amino acid sequence: (SEQ ID NO:1)

```
Ser Val Ser Glu Ile Gln Leu Met His Asn Leu
1               5                   10

Gly Lys His Leu Asn Ser Met Glu Arg Val Glu
            15                  20

Trp Leu Arg Lys Lys Leu Gln Asp Val His Asn
            25                  30

Phe Val Ala Leu Gly Ala Pro Leu Ala Pro Arg
            35                  40

Asp Ala Gly Ser Gln Arg Pro Arg Lys Lys Glu
45                  50                  55

Asp Asn Val Leu Val Glu Ser His Glu Lys Ser
                60                  65

Leu Gly Glu Ala Asn Lys Ala Asp Val Asn Val
            70                  75

Leu Thr Lys Ala Lys Ser Gln;
        80
``` b) recovering said antibody from said mammal;
   c) purifying said antibody by a combination of a positive adsorption to a PTH peptide consisting of an amino acid sequence consisting of $PTH_{1-34}$, and a negative adsorption to a PTH peptide having an amino acid sequence which starts at amino acid position 2 and ends at amino acid position 34 of said whole PTH.

2. The method of claim 1, wherein the positive adsorption to a PTH peptide in step c) is performed before the negative adsorption to a PTH peptide in step c).

3. The method of claim 1, wherein the positive adsorption to a PTH peptide in step c) is performed after the negative adsorption to a PTH peptide in step c).

* * * * *